(12) United States Patent
Yoshioka et al.

(10) Patent No.: US 8,992,905 B2
(45) Date of Patent: Mar. 31, 2015

(54) ORAL COMPOSITION CONTAINING INTERFERON-α

(75) Inventors: Kuniaki Yoshioka, Saitama (JP); Ko Sato, Saitama (JP); Toru Gotanda, Saitama (JP); Akira Ito, Hokkaido (JP); Emiko Isogai, Hokkaido (JP); Kazuaki Takehara, Aomori (JP); Nobutoshi Maehara, Saitama (JP)

(73) Assignees: Hokusan Co. Ltd., Hokkaido (JP); National Institute of Advanced Industrial Science and Technology, Tokyo (JP)

(*) Notice: Subject to any disclaimer, the term of this patent is extended or adjusted under 35 U.S.C. 154(b) by 1041 days.

(21) Appl. No.: 12/160,640

(22) PCT Filed: Jan. 12, 2007

(86) PCT No.: PCT/JP2007/050281
§ 371 (c)(1),
(2), (4) Date: Apr. 1, 2010

(87) PCT Pub. No.: WO2007/080942
PCT Pub. Date: Jul. 19, 2007

(65) Prior Publication Data
US 2010/0202982 A1    Aug. 12, 2010

(30) Foreign Application Priority Data

Jan. 12, 2006  (JP) ................ 2006-004526

(51) Int. Cl.
| A61K 38/21 | (2006.01) |
| A61K 38/00 | (2006.01) |
| A23K 1/16 | (2006.01) |
| A23K 1/18 | (2006.01) |
| A23L 1/30 | (2006.01) |
| A61K 9/00 | (2006.01) |

(52) U.S. Cl.
CPC ............. *A23K 1/1631* (2013.01); *A23K 1/1846* (2013.01); *A23L 1/30* (2013.01); *A61K 9/0063* (2013.01); *A61K 38/212* (2013.01)
USPC .................. 424/85.7; 424/85.4; 514/12.2

(58) Field of Classification Search
None
See application file for complete search history.

(56) References Cited

U.S. PATENT DOCUMENTS 5,017,371 A    5/1991  Cummins
5,019,382 A *  5/1991  Cummins, Jr. ............... 424/85.4
2005/0175724 A1  8/2005  Vandenberg

FOREIGN PATENT DOCUMENTS

| EP | 1260213 | 11/2001 |
| JP | 3504375 | 9/1991 |
| JP | 10273448 | 10/1998 |
| JP | 11239498 | 9/1999 |
| JP | 2001342199 | 12/2001 |
| JP | 2002034577 | 2/2002 |
| JP | 2002034590 | 2/2002 |
| JP | 2004018519 | 1/2004 |
| JP | 2005089301 | 4/2005 |
| JP | 2005522203 | 7/2005 |
| WO | 8906139 | 7/1989 |
| WO | 2006123164 | 11/2006 |

OTHER PUBLICATIONS

Igakusyoin Igakudaijiten, "Periodontal Disease", Mar. 1, 2003, 1:1032 and English translation, cited in Office Action for corresponding Japanese application dated Jan. 19, 2012.
Oromucosal Administration of Interferon to Humans, Manfred W. Beilharz et al., Pharmaceuticals 2010, 3, 323-344; doi: 10.3390/ph3020323; ISSN 1424-8247.
Grima et al., "Use of alpha-2 interferon in the local treatment of mucocutaneous lesions", C Ital Chemioter, English Translation, 1991, 38:211-2.
Jordan, "Three open-label studies of oral interferon alpha in the treatrrrent of HIV disease", Journal of the National Medical Association, 1994, 86(4):257-262.
Jordan, "Low-dose oral interferon-alpha: Effective prophylaxis for gingivitis and aphthous ulcers in AIDS patients", Journal of the National Medical Association, 1997, 89(10):647.
Khurshudian, "A pilot study to test the efficacy of oral administration of interferon-alpha lozenges to patients with Sjogren's syndrome", Oral Surgery, Oral Medicine, Oral Pathology, Jan. 2003, 95(1):38-44.
Mathur et al., "Interleukin-1 alpha, interleukin-8 and interferon-alpha levels in gingival crevicular fluid", Journal of Periodontal Research, Oct. 1996, 31(7):489-495.
Najera et al., "Prevalence of periodontal disease in patients with Sjogren's syndrome", Oral Surgery, Oral Medicine, Oral Pathology, Apr. 1997, 83(4):453-457.
Sakuta et al., "Dual regulatory effects of interferon-alpha, beta, and gamma on interleukin-8 gene expression by human gingival fibroblasts in culture upon stimulation with lipopolysaccharide from *Prevotella intermedia*, interleukin-1 alpha, or tumor necrosis factor-alpha", Journal of Dental Research, Aug. 1998, 77(8):1597-1605.
Tovey et al., "Oromucosal interferon therapy marked antiviral and antitumor activity", Journal of Interferon and Cytokine Research, 1999, 19:145-155.

(Continued)

*Primary Examiner* — Christine J Saoud
*Assistant Examiner* — Jegatheesan Seharaseyon
(74) *Attorney, Agent, or Firm* — Andrus Intellectual Property Law, LLP

(57) ABSTRACT

The present invention provides oral compositions which contain interferon α (IFNα) as an active ingredient for preventing and/or treating periodontal disease. The number of causative microorganisms of periodontal disease can be suppressed by administering the compositions into the oral cavity. IFNα of the present invention can produce a sufficient effect even when administered at a very low dose. Furthermore, the compositions of the present invention can also be readily administered to animals such as dogs by formulating them into feed or such.

3 Claims, 4 Drawing Sheets

(56) References Cited

OTHER PUBLICATIONS

European Search Report for EP07706628 dated Apr. 28, 2010.
English Abstract of EP1260213, published Nov. 27, 2001.
Cummins et al., "Treatment of Primary Sjogren's Syndrome With Low-Dose Human Interferon Alfa Administered by the Oromucosal Route: combined Phase III Results", Arthritis & Rheumatism, Aug. 15, 2003, 49(4):585-593.
Gilger et al., "Low-Dose Oral Administration of Interferon-alpha for the Treatment of Immune-Mediated Keratoconjunctivitis Sicca in Dogs", Journal Interferon and Cytokine Research, 1999, 19:901-905.
Gutterman, "Cytokine therapeutics: Lessons from interferon alpha", PNAS, Feb. 1994, 91:1198-1205.
Kaser et al., "Interferon-alpha in inflammation and immunity", Cellular and Molecular Biology, 2001, 47(4):609-617.
Lecce et al., "Treatment of rotavirus infection in neonate and weanling pigs using natural human interferon alpha", Molecular Biotherapy Journal, Dec. 1990, 2:211-216.
Lecciones et al., "A Pilot Double-Blind, Randomized, and Placebo-Controlled Study of Orally Administered IFN-alpha-n1 (Ins) in Pediatric Patients with Measels", Journal fo Interferon and Cytokine Research, 1998, 18:647-652.
Ohtsuka et al,. "Peripheral Mononuclear Cell Response in Japanese Black Calves after Oral Administration of IFN-alpha", Journal of Veterinary Medical Science, Oct. 2006, 68(120:1063-1067.
Palomba et al., "Oral use of interferon therapy in cervical human papillomavirus infection", La Clinica Terapeutica, 2000, 151(Suppl 1):59-61.
Pihlstrom et al., "Periodontal disease", The Lancet, Nov. 19, 2005, 366(9499):1809-1820.
Satoh et al., "Suppression of Late Asthmatic Response by Low-Dose Oral Administration of Interferon-beta in the Guinea Pig Model of Asthma", Journal of Interferon and Cytokine Research, 1999, 19:887-894.
Shiozawa et al., "Single-Blinded Controlled Trial of Low-Dose Oral IFN-alpha for the Treatment of Xerostomia in Patients with Sjogren's Syndrome", Journal of Interferon and Cytokine Research, 1998, 18:255-262.
Ship et al., "Treatment of Primary Sjogren's Syndrome with Low-dose Natural Human Interferon-alpha Administered by the Oral Mucosal Route: A Phase II Clinical Trial", Journal of Interferon and Cytokine Research, 1999, 19:943-951.
Tompkins, "Immunomodulation and Therapeutic Effects of the Oral Use of Interferon-alpha: Mechanism of Action", Journal of Interferon and Cytokine Research, 1999, 19:817-828.
Young et al., "Low-dose oral administration of human interferon alpha can control the development of *Theileria parva* infection in cattle", Parasitology, 1990, 101:201-209.
International Search Report for PCT/JP2007/050281 dated Apr. 2, 2007.
Written Opinion for PCT/JP2007/050281 dated Apr. 2, 2007.
Abstract for JP11239498, published Sep. 7, 1999.
Abstract for JP2001342199, published Dec. 11, 2001.
Abstract for JP2002034577, published Feb. 5, 2002.
Abstract for JP2002034590, published Feb. 5, 2002.
Abstract for JP2004018519, published Jan. 22, 2004.
Abstract for JP2005089301, published Apr. 7, 2005.

\* cited by examiner

```
        10         20         30         40         50         60         70         80         90
ATGGCCCTGCCCTGCTCTTCGGTGGCCCTGGTGCTCAGCTGCCACTCCCTGTGTTGTCTGGCTTGCGACCTGCCCGACACCCAC
 M   A   L   P   C   S   F   S   V   A   L   V   L   S   C   H   S   L   C   C   L   A  │C   D   L   P   D   T   H 100        110        120        130        140        150        160        170        180
AGCCTGCGCAACTGGAGAGGGTCCTGACGTTCTGGGACGGCTCTCCTGACTTCCGGACACTACACCTGACTTTGCC
 S   L   R   N   W   R   V   L   T   L   L   G   Q   M   R   R   L   S   A   S   S   C   D   H   Y   T   T   D   F   A 190        200        210        220        230        240        250        260        270
TTCCCCAAGGAACTGTTTGATGGCCAGCGTCTCCAGGAGGCGCAAGCCCTCTGTGTGGTCCACGTGATGACCCAGAAGGTCTTCCACCTC
 F   P   K   E   L   F   D   G   Q   R   L   Q   E   A   Q   A   L   S   V   V   H   V   M   T   Q   K   V   F   H   L 280        290        300        310        320        330        340        350        360
TTCTGCACGAACATGTCCTCTGCTCCTTGGAACATGACCCTCCTGGAAGAATTGTGCTCTGGGGCTCTCTGAGCAGCTGGATGACCTGGAT
 F   C   T   N   M   S   S   A   P   W   N   M   T   L   E   E   L   C   S   G   L   S   E   Q   L   D   D   L   D 370        380        390        400        410        420        430        440        450
GCCTGTCCCCTGCAGGAGGCTGGCCTGGCTGAAGACTCCACCCTGAGGACTTACTTCCAAAGGATCTCCCTC
 A   C   P   L   Q   E   A   G   L   A   E   T   P   L   M   H   E   D   S   T   L   R   T   Y   F   Q   R   I   S   L 460        470        480        490        500        510        520        530        540
TACCTGCAAGACAGGAACCACAGCCCGTGCCTGGAGATGGTCCGAGCAGAAATCGGAGAGATCCTTCTTCCTTCCTTGACCATCTTGCAA
 Y   L   Q   D   R   N   H   S   P   C   A   W   E   M   V   R   A   E   I   G   R   S   F   F   S   L   T   I   L   Q 550        560        570        580
GAAAGAGTAAGGAGGAGGAAACATCATCATCATCATCATTGA           (SEQ ID NO: 1)
 E   R   V   R   R   R   K   H   H   H   H   H   H   *                 (SEQ ID NO: 2)
```

FIG. 1

```
SEQUENCE LISTING

<160> NUMBER OF SEQ ID NOS: 8

<210> SEQ ID NO 1
<211> LENGTH: 582
<212> TYPE: DNA
<213> ORGANISM: Canis sp.
<220> FEATURE:
<221> NAME/KEY: CDS
<222> LOCATION: (1)..(579)

<400> SEQUENCE: 1 atg gcc ctg ccc tgc tcc ttc tcg gtg gcc ctg gtg ctg ctc agc tgc      48
Met Ala Leu Pro Cys Ser Phe Ser Val Ala Leu Val Leu Leu Ser Cys
1               5                   10                  15 cac tcc ctg tgc tgt ctg gct tgc gac ctg ccc gac acc cac agc ctg      96
His Ser Leu Cys Cys Leu Ala Cys Asp Leu Pro Asp Thr His Ser Leu
                20                  25                  30 cgc aac tgg agg gtc ctg acg ctc ctg gga cag atg agg aga ctc tcc     144
Arg Asn Trp Arg Val Leu Thr Leu Leu Gly Gln Met Arg Arg Leu Ser
            35                  40                  45 gcc agc tct tgt gac cac tac acc act gac ttt gcc ttc ccc aag gaa     192
Ala Ser Ser Cys Asp His Tyr Thr Thr Asp Phe Ala Phe Pro Lys Glu
        50                  55                  60
```

```
ctg ttt gat ggc cag cgg ctc cag gag gcg caa gcc ctc tct gtg gtc      240
Leu Phe Asp Gly Gln Arg Leu Gln Glu Ala Gln Ala Leu Ser Val Val
 65                  70                  75                  80 cac gtg atg acc cag aag gtc ttc cac ctc ttc tgc acg aac atg tcc      288
His Val Met Thr Gln Lys Val Phe His Leu Phe Cys Thr Asn Met Ser
                 85                  90                  95 tct gct cct tgg aac atg acc ctc ctg gaa gaa ttg tgc tcg ggg ctc      336
Ser Ala Pro Trp Asn Met Thr Leu Leu Glu Glu Leu Cys Ser Gly Leu
            100                 105                 110 tct gag cag ctg gat gac ctg gat gcc tgt ccc ctg cag gag gca ggg      384
Ser Glu Gln Leu Asp Asp Leu Asp Ala Cys Pro Leu Gln Glu Ala Gly
        115                 120                 125 ctg gcc gag acc ccc ctc atg cat gaa gac tcc acc ctg agg acc tac      432
Leu Ala Glu Thr Pro Leu Met His Glu Asp Ser Thr Leu Arg Thr Tyr
    130                 135                 140 ttc caa agg atc tcc ctc tac ctg caa gac agg aac cac agc ccg tgt      480
Phe Gln Arg Ile Ser Leu Tyr Leu Gln Asp Arg Asn His Ser Pro Cys
145                 150                 155                 160 gcc tgg gag atg gtc cga gca gaa atc ggg aga tcc ttc ttc tcc ttg      528
Ala Trp Glu Met Val Arg Ala Glu Ile Gly Arg Ser Phe Phe Ser Leu
                165                 170                 175 acc atc ttg caa gaa aga gta agg agg agg aaa cat cat cat cat cat      576
Thr Ile Leu Gln Glu Arg Val Arg Arg Arg Lys His His His His His
            180                 185                 190 cat tga                                                               582
His

<210> SEQ ID NO 2
<211> LENGTH: 193
<212> TYPE: PRT
<213> ORGANISM: Canis sp.

<400> SEQUENCE: 2

Met Ala Leu Pro Cys Ser Phe Ser Val Ala Leu Val Leu Leu Ser Cys
 1               5                  10                  15

His Ser Leu Cys Cys Leu Ala Cys Asp Leu Pro Asp Thr His Ser Leu
             20                  25                  30

Arg Asn Trp Arg Val Leu Thr Leu Leu Gly Gln Met Arg Arg Leu Ser
         35                  40                  45

Ala Ser Ser Cys Asp His Tyr Thr Thr Asp Phe Ala Phe Pro Lys Glu
     50                  55                  60

Leu Phe Asp Gly Gln Arg Leu Gln Glu Ala Gln Ala Leu Ser Val Val
 65                  70                  75                  80

His Val Met Thr Gln Lys Val Phe His Leu Phe Cys Thr Asn Met Ser
                 85                  90                  95

Ser Ala Pro Trp Asn Met Thr Leu Leu Glu Glu Leu Cys Ser Gly Leu
            100                 105                 110

Ser Glu Gln Leu Asp Asp Leu Asp Ala Cys Pro Leu Gln Glu Ala Gly
        115                 120                 125

Leu Ala Glu Thr Pro Leu Met His Glu Asp Ser Thr Leu Arg Thr Tyr
    130                 135                 140

Phe Gln Arg Ile Ser Leu Tyr Leu Gln Asp Arg Asn His Ser Pro Cys
145                 150                 155                 160

Ala Trp Glu Met Val Arg Ala Glu Ile Gly Arg Ser Phe Phe Ser Leu
                165                 170                 175
```

```
Thr Ile Leu Gln Glu Arg Val Arg Arg Lys His His His His
        180             185                 190

His

<210> SEQ ID NO 3
<211> LENGTH: 573
<212> TYPE: DNA
<213> ORGANISM: Canis sp.
<220> FEATURE:
<221> NAME/KEY: CDS
<222> LOCATION: (13)..(573)
<220> FEATURE:
<221> NAME/KEY: sig_peptide
<222> LOCATION: (13)..(81)
<220> FEATURE:
<221> NAME/KEY: mat_peptide
<222> LOCATION: (82)..(573)

<400> SEQUENCE: 3
gcaggatcca cg atg gcc ctg ccc tgc tcc ttc tcg gtg gcc ctg gtg ctg     51
           Met Ala Leu Pro Cys Ser Phe Ser Val Ala Leu Val Leu
               -20                 -15 ctc agc tgc cac tcc ctg tgc tgt ctg gct tgc gac ctg ccc gac acc      99
Leu Ser Cys His Ser Leu Cys Cys Leu Ala Cys Asp Leu Pro Asp Thr
-10              -5              -1  1               5 cac agc ctg cgc aac tgg agg gtc ctg acg ctc ctg gga cag atg agg    147
His Ser Leu Arg Asn Trp Arg Val Leu Thr Leu Leu Gly Gln Met Arg
            10                  15                  20 aga ctc tcc gcc agc tct tgt gac cac tac acc act gac ttt gcc ttc    195
Arg Leu Ser Ala Ser Ser Cys Asp His Tyr Thr Thr Asp Phe Ala Phe
        25                  30                  35 ccc aag gaa ctg ttt gat ggc cag cgg ctc cag gag gcg caa gcc ctc    243
Pro Lys Glu Leu Phe Asp Gly Gln Arg Leu Gln Glu Ala Gln Ala Leu
    40                  45                  50 tct gtg gtc cac gtg atg acc cag aag gtc ttc cac ctc ttc tgc acg    291
Ser Val Val His Val Met Thr Gln Lys Val Phe His Leu Phe Cys Thr
55                  60                  65                  70 aac atg tcc tct gct cct tgg aac atg acc ctc ctg gaa gaa ttg tgc    339
Asn Met Ser Ser Ala Pro Trp Asn Met Thr Leu Leu Glu Glu Leu Cys
                75                  80                  85 tcg ggg ctc tct gag cag ctg gat gac ctg gat gcc tgt ccc ctg cag    387
Ser Gly Leu Ser Glu Gln Leu Asp Asp Leu Asp Ala Cys Pro Leu Gln
            90                  95                  100 gag gca ggg ctg gcc gag acc ccc ctc atg cat gaa gac tcc acc ctg    435
Glu Ala Gly Leu Ala Glu Thr Pro Leu Met His Glu Asp Ser Thr Leu
        105                 110                 115 agg acc tac ttc caa agg atc tcc ctc tac ctg caa gac agg aac cac    483
Arg Thr Tyr Phe Gln Arg Ile Ser Leu Tyr Leu Gln Asp Arg Asn His
    120                 125                 130 agc ccg tgt gcc tgg gag atg gtc cga gca gaa atc ggg aga tcc ttc    531
Ser Pro Cys Ala Trp Glu Met Val Arg Ala Glu Ile Gly Arg Ser Phe
135                 140                 145                 150 ttc tcc ttg acc atc ttg caa gaa aga gta agg agg agg aaa            573
Phe Ser Leu Thr Ile Leu Gln Glu Arg Val Arg Arg Arg Lys
                155                 160

<210> SEQ ID NO 4
<211> LENGTH: 187
<212> TYPE: PRT
<213> ORGANISM: Canis sp.
```

<400> SEQUENCE: 4

```
Met Ala Leu Pro Cys Ser Phe Ser Val Ala Leu Val Leu Leu Ser Cys
            -20                 -15                 -10

His Ser Leu Cys Cys Leu Ala Cys Asp Leu Pro Asp Thr His Ser Leu
         -5              -1   1               5

Arg Asn Trp Arg Val Leu Thr Leu Leu Gly Gln Met Arg Arg Leu Ser
 10              15                  20                  25

Ala Ser Ser Cys Asp His Tyr Thr Thr Asp Phe Ala Phe Pro Lys Glu
             30                  35                  40

Leu Phe Asp Gly Gln Arg Leu Gln Glu Ala Gln Ala Leu Ser Val Val
             45                  50                  55

His Val Met Thr Gln Lys Val Phe His Leu Phe Cys Thr Asn Met Ser
             60                  65                  70

Ser Ala Pro Trp Asn Met Thr Leu Leu Glu Glu Leu Cys Ser Gly Leu
 75                  80                  85

Ser Glu Gln Leu Asp Asp Leu Asp Ala Cys Pro Leu Gln Glu Ala Gly
 90                  95                 100                 105

Leu Ala Glu Thr Pro Leu Met His Glu Asp Ser Thr Leu Arg Thr Tyr
                110                 115                 120

Phe Gln Arg Ile Ser Leu Tyr Leu Gln Asp Arg Asn His Ser Pro Cys
            125                 130                 135

Ala Trp Glu Met Val Arg Ala Glu Ile Gly Arg Ser Phe Phe Ser Leu
            140                 145                 150

Thr Ile Leu Gln Glu Arg Val Arg Arg Lys
            155                 160
```

<210> SEQ ID NO 5
<211> LENGTH: 22
<212> TYPE: DNA
<213> ORGANISM: Artificial
<220> FEATURE:
<223> OTHER INFORMATION: Artificially synthesized primer sequence for
      canine IFN-alpha 4
<220> FEATURE:
<221> NAME/KEY: misc_feature
<222> LOCATION: (4)..(9)
<223> OTHER INFORMATION: BamHI recognition site

<400> SEQUENCE: 5
gcaggatcca cgatggccct gc                                              22

<210> SEQ ID NO 6
<211> LENGTH: 54
<212> TYPE: DNA
<213> ORGANISM: Artificial
<220> FEATURE:
<223> OTHER INFORMATION: Artificially synthesized primer sequence for
      canine IFN-alpha 4
<220> FEATURE:
<221> NAME/KEY: misc_feature
<222> LOCATION: (4)..(9)
<223> OTHER INFORMATION: BamHI recognition site
<220> FEATURE:
<221> NAME/KEY: misc_feature
<222> LOCATION: (14)..(34)
<223> OTHER INFORMATION: His tag coding sequence

<400> SEQUENCE: 6
gctggatccg tcaatgatga tgatgatgat gatgtttcct cctccttact cttc           54

-continued

```
<210> SEQ ID NO 7
<211> LENGTH: 4
<212> TYPE: PRT
<213> ORGANISM: Artificial
<220> FEATURE:
<223> OTHER INFORMATION: Artificially added ERR signal sequence

<400> SEQUENCE: 7

Lys Asp Glu Leu
1

<210> SEQ ID NO 8
<211> LENGTH: 4
<212> TYPE: PRT
<213> ORGANISM: Artificial
<220> FEATURE:
<223> OTHER INFORMATION: Artificially added ERR signal sequence

<400> SEQUENCE: 8

Arg Asp Glu Leu
1
```

ORAL COMPOSITION CONTAINING INTERFERON-α

CROSS REFERENCE TO RELATED APPLICATIONS

This application is the U.S. national stage application of international application No. PCT/JP2007/050281, filed on Jan. 12, 2007, which international application was published on Jul. 19, 2007, as international publication No. WO 2007/080942 in the Japanese language. The international application claims benefit of priority to Japanese application No. JP 2006-004526, filed on Jan. 12, 2006, which international application and Japanese application are incorporated herein by reference in their entireties.

TECHNICAL FIELD

The present invention relates to interferon α-comprising compositions for preventing and/or treating periodontal diseases and methods thereof.

BACKGROUND ART

The importance of oral hygiene has grown with the progression in aging. For example, the prevention and treatment of dental decays (cavity) and periodontal diseases is an important objective in oral hygiene. Aging is causing similar problems in pet animals such as dogs and cats as in human. Specifically, the establishment of techniques for preventing or treating periodontal diseases in pet animals has also become an important task. In general, keeping the mouth clean by toothbrushing is believed to be an important daily habit to prevent periodontal diseases and dental decays. However, brushing an animal's teeth is not always easy. Thus, it can also be said that the technology for preventing or treating periodontal diseases in animals is more important than that for humans.

Gingivitis and periodontitis are representative oral diseases, and collectively called "periodontal diseases". Gingivitis is a disease caused by bacteria in plaques (dental plaques) accumulated on the surface of teeth and periodontal tissues. Gingival swelling and bleeding are observed, but not alveolar bone absorption. In most cases, gingivitis is curable.

In periodontitis, inflammation also spreads to the periodontal membrane and alveolar bone. Periodontitis is a pathological change that results in the disruption of periodontal tissues such as the periodontal membrane and alveolar bone. To date, it is difficult to therapeutically restore destroyed periodontal tissues. Periodontitis is a severe inflammatory disease that ultimately results in tooth exfoliation. Depending on the degree of severity, periodontitis worsens bad breath and causes bleeding, and contact with the teeth becomes unpleasant. In more severe cases, oral pathogenic bacteria circulate within the body via blood stream, and the effects are occasionally observed in the heart, kidney, and others. Multiple factors are suggested to cause periodontal disease. From the point of infection by plaque pathogenic bacteria, periodontal disease is a common disease to human and animals.

The most common causative bacteria of the periodontal disease are black-pigmented Gram-negative anaerobic bacteria. This group of bacteria was formerly classified into the genus *Bacteroides*, but is currently grouped into the genera *Porphyromonas* and *Prevotella*. Although bacterial species that cause the periodontal disease in different animals are slightly different, they all cause the disease in human, dog, cat, sheep, rat, and other animals. In dogs and cats, the proportion of the genus *Porphyromonas* in bacterial flora of dental plaques occasionally reaches 80%. The most frequently isolated bacterial species is *P. gingivalis*. *P. endodontalis*, *P. circumdentaria*, *P. canoris*, *P. salivosa*, and the like are also often isolated. Additional new bacterial species are expected to be isolated in the future.

About 80% of family dogs are believed to have periodontitis. If periodontal disease is not treated, tooth pain and extraction may occur, which significantly reduce the quality of life (QOL) for the pet. During the past several years, chews (gums for pets), treats (snacks), pet food, and the like, containing components for improving their oral hygiene were commercialized one after another. This suggests the growing interest of pets' owners in the periodontal disease of their pets.

Actually, commercial products that are intended to prevent periodontal disease are sold on the market, reflecting such owners' interest. For example, pet food formulated with dietary fibers is assumed to have the effect of preventing periodontal disease by suppressing the deposition of dental plaque and calculus by using the mechanical removing action of mastication. "Hill's Prescription Diet t/d" (trade name) is a pet food product formulated with dietary fibers. Dog tooth paste and the like formulated with enzymes aiming at plaque control have also been developed. Furthermore, there are a supplement (trade name: "Xylitol C") and pet beverages aiming at oral care that use the synergistic effects of active ingredients such as Biofermentics, vitamin C, oyster extract, xylitol, Sunphenon, and catechin.

In current veterinary clinical practice, periodontal disease is treated by the following methods:

(1) removal of plaque which is the major cause of this disease;

(2) dental scaling (removal of dental calculus);

(3) tooth extraction; etc.

Specifically, the prevention of dental calculus deposition and plaque control are important as post-therapeutic care or preventive method for periodontal disease. Thus, particular formulae of dry pet food having the effect of mechanical removal of dental calculus are one of the effective measures to date. Alternatively, brushing using pet tooth powder is also expected to have therapeutic and preventive effects.

Patent Document 1: Japanese Patent Application Kokai Publication No. (JP-A) 2002-34590 (unexamined, published Japanese patent application)

Patent Document 2: JP-A (Kokai) 2002-34577

Patent Document 3: JP-A (Kokai) 2001-342199

Patent Document 4: JP-A (Kokai) H11-239498

Patent Document 5: JP-A (Kokai) 2005-89301

Non-patent Document 1: Cummins, M. J., Arthritis Rheum., 2003; 49(4): p585-593

Non-patent Document 2: Shiozawa, S., J. Interferon Cytokine Res., 1998; 18(4): p255-262

Non-patent Document 3: Ship, J. A., J. Interferon Cytokine Res., 1999; 19(8): p943-951

Non-patent Document 4: Gilger, B. C., J. Interferon Cytokine Res., 1999; 19(8): p901-905

Non-patent Document 5: Satoh, Y., J. Interferon Cytokine Res., 1999; 19(8): p887-894

Non-patent Document 6: Palomba, M., Clin. Ter., 2000; 151(1 Suppl. 1): p59-61

Non-patent Document 7: Lecciones, J. A., J. Interferon Cytokine Res., 1998; 18(9): p647-652

Non-patent Document 8: Lecce, J. G, Mol. Biother., 1990; 2(4): p211-216

Non-patent Document 9: Young, A. S., Parasitology, 1990; 101(2): p201-209
Non-patent Document 10: Tompkins, W. A., J. Interferon Cytokine Res., 1999; 19: p817-828
Non-patent Document 11: Ohtsuka, H., J. Vet. Med. Sci., 2006; 68(10): p1063-1067

DISCLOSURE OF THE INVENTION

Problems to be Solved by the Invention

It is evident that dental plaque and calculus are a cause of periodontal disease, and thus their removal is an important task for treating and preventing the disease. The removal of dental plaque and calculus can be expected to have the effect of preventing periodontal disease. However, its therapeutic effect on periodontal disease is not satisfactory. For example, the therapeutic effect of dental plaque removal on already advanced inflammation is indirect. Thus, more effective methods for treating periodontal disease will be useful.

Furthermore, bacteria causing periodontal disease cannot be removed from the oral cavity by removing dental plaque. Specifically, the "nest" of pathogenic bacteria is removed by removing dental plaque and calculus. Indeed, dental plaque and calculus are the major cause of periodontal disease. However, causative bacteria are also present at sites other than the "nest" in the oral cavity. In other words, the bacteria themselves cannot be suppressed by removing dental plaque. If methods having direct effects on causative bacteria of periodontal disease are provided, stronger preventive effects can be expected.

Furthermore, brushing, which is effective for removing dental plaque and calculus, may be difficult in some animals. Thus, it would be useful if periodontal disease can be prevented or treated without brushing. An objective of the present invention is to provide novel techniques for preventing and/or treating periodontal disease.

Means for Solving the Problems

The present inventors speculated that interferon (hereinafter abbreviated as "IFN") was effective to treat or prevent periodontal disease. IFN is a cytokine having pleiotropic biological activities such as antiviral activity, cell growth-suppressing activity, and immune response-regulating activity. IFN has already been clinically applied as an antiviral agent in the treatment of chronic type-C hepatitis. In addition, IFNα has also been used as an antitumor agent in the treatment of chronic myelocytic leukemia, renal cell carcinoma, and the like.

In these therapeutic methods, administration of high doses of IFNα is a standard method of administration. For example, an induction therapy is used for human, which injects IFNα at a daily dose of 6 to 10 MIU every day for the first two or three weeks and then three times a week for 22 weeks. Injectable interferon preparations are also commercialized in the veterinary field. The injectable feline interferon-ω preparation Intercat™ (trade name, Toray Industries) is a therapeutic agent for feline calicivirus infection. Furthermore, as a new agent for industrial animals, oral interferon preparation Bimuron™ (trade mark, BioVet) for bovine rotavirus infection has recently been put to practical use (JP-A (Kokai) 2005-89301). Bimuron™ brand oral interferon preparation is a powder preparation formulated with naturally-occurring human IFNα.). Bimuron™ brand oral interferon preparation was proven to produce the effect of suppressing diarrhea and virus discharge accompanied by bovine rotavirus infection, when formulated into feed or the like and administered at a minute amount of about 0.5 IU/day/kg body weight.

However, the effect of these IFNα preparations on periodontal disease is unknown. The present inventors discovered that periodontal disease can be prevented and treated by administering, in particular, IFNα into the oral cavity, and thus completed the present invention. Specifically, the present invention provides the following compositions and methods:

[1] a composition for oral administration to prevent and/or treat periodontal disease, which comprises interferon α as an active ingredient;
[2] the composition of [1], wherein the periodontal disease is a periodontal disease in a mammal;
[3] the composition of [2], wherein the mammal is a dog or cat;
[4] the composition of [2], wherein the mammal is a human;
[5] the composition of [1], which comprises interferon α and a chewable carrier;
[6] the composition of [5], wherein the chewable carrier is food;
[7] the composition of [6], which is a chewable tablet or chewing gum;
[8] the composition of [1], which comprises interferon α and a paste carrier;
[9] the composition of [1], which is formulated with interferon α at 0.05 to 2,500 LU/day/kg body weight;
[10] the composition of [8], which is formulated with interferon α at 0.1 to 1,500 LU/day/kg body weight;
[11] a method for preventing and/or treating periodontal disease in a mammal, which comprises the step of administering interferon α into its oral cavity;
[12] the method of [11], which comprises the step of administering a composition comprising interferon α and a chewable carrier into the oral cavity;
[13] the method of [11], which comprises the step of applying a composition comprising interferon α and a paste carrier on an oral tissue;
[14] the method of [11], wherein the mammal is a nonhuman mammal;
[15] the method of [14], wherein the mammal is a dog or cat;
[16] the method of [11], wherein interferon α is administered at 0.05 to 2,500 LU/day/kg body weight;
[17] the method of [16], wherein interferon α is administered at 0.1 to 1,500 LU/day/kg body weight;
[18] a pharmaceutical composition for oral administration to prevent and/or treat periodontal disease in a mammal, which comprises interferon α and a pharmaceutically acceptable carrier;
[19] the pharmaceutical composition of [18], wherein the pharmaceutically acceptable carrier is a chewable carrier;
[20] the pharmaceutical composition of [18], wherein the pharmaceutically acceptable carrier is a paste carrier;
[21] the pharmaceutical composition of [18], which is formulated with interferon α at 0.05 to 2,500 LU/day/kg body weight;
[22] the pharmaceutical composition of [21], which is formulated with interferon α at 0.1 to 1,500 LU/day/kg body weight;
[23] a food composition, which is formulated with interferon α at 0.05 to 2,500 LU/day/kg body weight;
[24] the food composition of [23], which is formulated with interferon α at 0.1 to 1,500 LU/day/kg body weight;
[25] a feed composition, which is formulated with interferon α at 0.05 to 2,500 LU/day/kg body weight; and

[26] the feed composition of [25], which is formulated with interferon α at 0.1 to 1,500 LU/day/kg body weight.

Effects of the Invention

Periodontal disease can be prevented and treated by administering into the oral cavity the oral compositions of the present invention for preventing or treating periodontal disease. Specifically, remarkable suppression of causative microorganisms of periodontal disease by administering the oral compositions of the present invention was demonstrated. The removal of dental plaque and calculus, which is believed to be effective for preventing periodontal disease in general, is intended to remove nests of the causative microorganisms of periodontal disease. In other words, the effect of removing dental plaque and calculus is indirect for both prevention and treatment. In the present invention, the preventive and therapeutic effects on periodontal disease are produced by suppressing the number of causative microorganisms of the periodontal disease. Thus, the preventive or therapeutic effect of the present invention can be assumed to result from the direct action on the cause of periodontal disease.

It was indeed confirmed in the Examples that the therapeutic agents of the present invention for periodontal disease alleviated the symptoms of periodontal disease in the periodontal disease model animals. This result supports that the present invention established a method for active treatment of periodontal disease.

As described above, unlike brushing, the methods of the present invention for preventing or treating periodontal disease suppress causative bacteria of the periodontal disease. Thus, periodontal disease can be prevented or treated more certainly by combining the preventive or therapeutic methods of the present invention with the removal of dental plaque and calculus by brushing.

Furthermore, the compositions of the present invention for preventing or treating periodontal disease can also be readily administered to animals. For example, when added to feed, IFNα can be simply administered to the oral cavities of animals through their feeding behaviors. Administration of the compositions of the present invention can be achieved in a very convenient way, while tooth and gingival brushing is difficult in some animals. Thus, the present invention is also useful in preventing or treating periodontal disease in animals.

Furthermore, the oral compositions of the present invention can produce the strong effect of preventing or treating periodontal disease with a very low dose of formulated IFNα. Since the dosage of IFNα can be reduced, the risk of side effects which may be caused by high-dose IFNα administration can be avoided. In addition, it is advantageous for providing low-price products that the amount of IFNα used is small, because IFNα is assumed to account for the majority of costs of the final products.

Alternatively, the number of oral pathogenic bacteria can be suppressed by administering antibiotics, for example. However, periodontal disease is a disease that needs to be prevented continuously through the entire human or animal life. It is not realistic to constantly administer antibiotics to human, or industrial or pet animals for the purpose of preventing or treating such disease. The problem of safety is a concern in antibiotics use. In contrast, the present invention can produce the preventive and therapeutic effects by administering a small dose of IFNα into the oral cavity. The administration of a small dose of IFNα is a administration method proven to be safe. For example, the therapeutic agent for bovine rotavirus has already been put to practical use. Thus, the preventive or therapeutic agents of the present invention are also advantageous in safety.

BRIEF DESCRIPTION OF THE DRAWINGS

FIG. 1 is a diagram showing the nucleotide sequence of cDNA fragment inserted into the plasmid pAcYM1 as described in Example 1 and the amino acid sequence encoded thereby. The region boxed with solid line is the signal peptide region of CaIFNα4; double underlines indicate glycosylation sites; the region boxed with dotted line is the histidine tag attached to CaIFNα4.

BEST MODE FOR CARRYING OUT THE INVENTION

Figure 2:
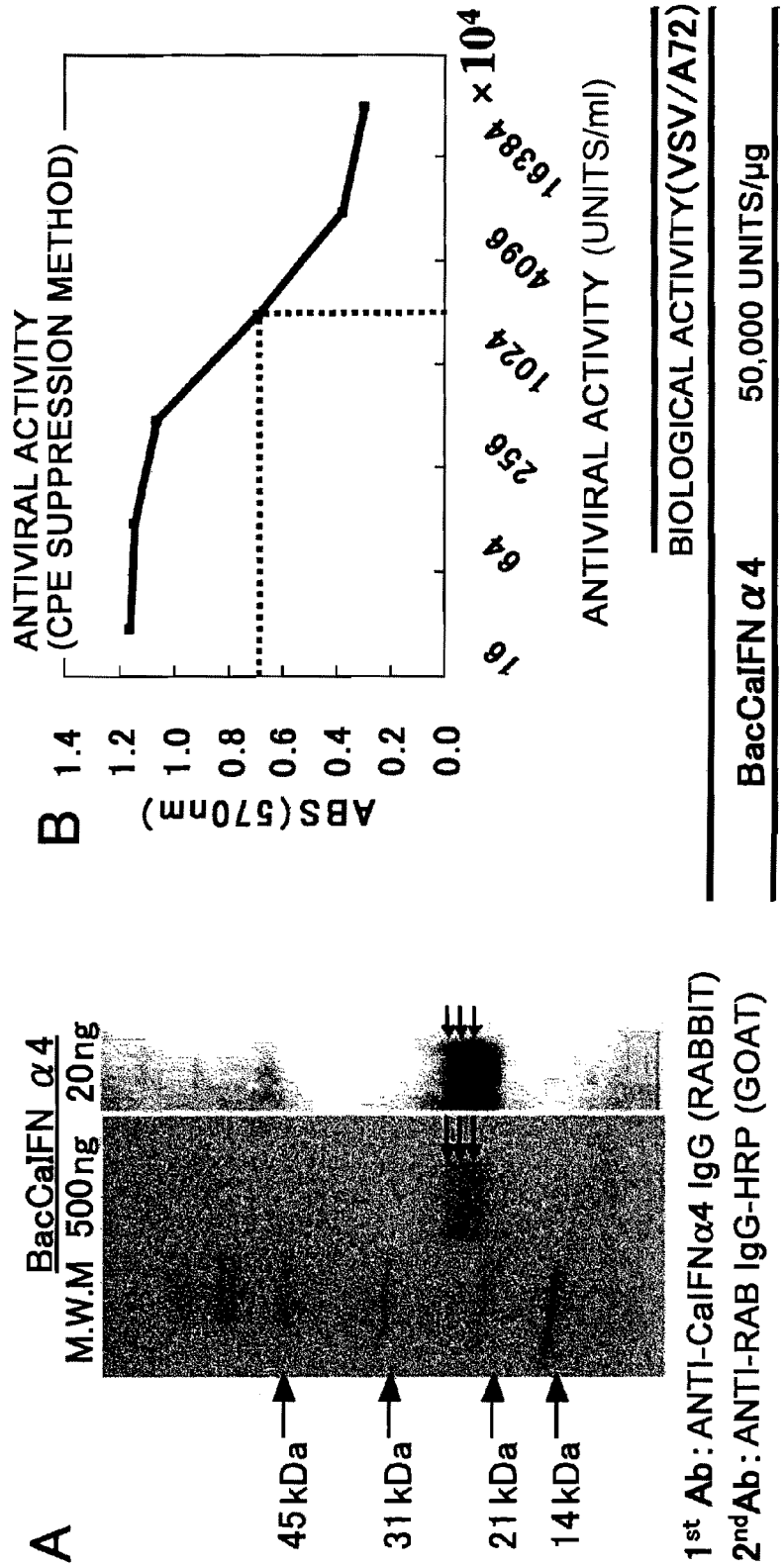
FIG. 2A is a photograph showing the detection of purified BacCaIFNα4 protein by CBB staining and Western blotting.
FIG. 2B is a graph showing the assessment of the antiviral activity of purified BacCaIFNα4 protein by the CPE suppression method. In this graph, the vertical axis indicates absorbance at 570 nm, and the horizontal axis indicates the antiviral activity (LU/ml) of IFNα.

The present invention relates to oral compositions which comprise IFNα as an active ingredient for preventing and/or treating periodontal disease. The oral compositions of the present invention can be produced by combining interferon α with biologically acceptable carriers.

Interferon is a protein with a molecular weight of about 20 kDa that is secreted in the animal body upon viral infection or such. Mammals have three types of INFs: α, β, and γ. Of these, α and β are structurally similar to each other. For example, in human and mouse, α and β exhibit about 40% and 35% homology at the nucleotide and amino acid sequence levels, respectively. These IFNs are collectively called type-I IFN. In addition to the antiviral activity, type-I IFN has been found to have the following activities:

cell growth-suppressing activity;
antitumor activity;
activity of activating immune cells such as macrophages; and
immune response-regulating activity.

IFNα of mammals such as human and mouse are polymorphic. For example, a group of 15 or more homologous (85% or higher) genes have been found in human. The major characteristic of the IFNα gene is that it has no intron and exists in multiple copies as polymorphic variants in the genome.

The IFNα of the present invention includes all the subtypes derived from such polymorphic variants. In addition, proteins comprising an amino acid sequence with addition, deletion, substitution, or insertion of one or multiple amino acids in the amino acid sequence of such a subtype and having the biological activity equivalent to or higher than that of IFNα can also be used as IFNα of the present invention. IFNα derived from any animal species can be used as IFNα of the present invention. According to the animal species to be administered, IFNα derived from the same animal species is preferably used.

Alternatively, IFNα derived from other species may be used as long as it can produce the effect of preventing or treating periodontal disease. For example, IFNα subtypes derived from the species listed below are known. The nucleotide and amino acid sequences of the respective subtypes of naturally-occurring IFNα are available under the GenBank accession numbers indicated below. In any species, there is a possibility that new subtypes will be discovered in addition to these subtypes. Any subtype newly identified in the future can also be used as IFNα of the present invention as long as it has the required activity.

In general, the amino acid sequences represented by these accession numbers contain signal sequences. When an amino acid sequence contains a signal sequence, a mature protein from which the signal sequence has been removed is used as IFNα of the present invention. If a precursor protein consisted of an amino acid sequence with the whole or a portion of signal sequence has IFNα biological activities, it can also be used as IFNα. Alternatively, precursor proteins that can acquire IFNα biological activities when the whole or a portion of signal sequence is removed after administration can also be used as IFNα of the present invention.

| Canine IFNα (8 subtypes) | | |
|---|---|---|
| CaIFN-a1: M28624 | CaIFN-a2: M28625 | CaIFN-a3: O97945 |
| CaIFN-a4: AB102731 | CaIFN-a5: AB125934 | CaIFN-a6: AB125935 |
| CaIFN-a7: AB125936 | CaIFN-a8: AB125937 | |
| Feline IFNα (14 subtypes) | | |
| FeIFN-w: E02521 | FeIFN-a1: AY117395 | FeIFN-a2: AY117394 |
| FeIFN-a3: AY117393 | FeIFN-a5: AY117392 | FeIFN-a6: AY117391 |
| FeIFN-a7: AB094996 | FeIFN-a8: AB094997 | FeIFN-a9: AB094998 |
| FeIFN-a10: AB094999 | FeIFN-a11: AB095000 | FeIFN-a12: AB095001 |
| FeIFN-a13: AB095002 | FeIFN-a14: AB095003 | |
| Rodent IFNα (8 subtypes) | | |
| D00460, M13660, M13710, X01969, X01971, X01972, X01973, X01974 | | |
| Bovine IFNα (8 subtypes) | | |
| M10952, M10953, M10954, M10955, M11001, X93087, X93088, X93089 | | |
| Porcine IFNα | | |
| IFN-a1: X57191.1 | | |
| Human IFNα (21 subtypes) | | |
| HuIFN-a1: DQ185447 | HuIFN-a2: NM000605 | HuIFN-a3: E00176 |
| HuIFN-a4: NM021068 | HuIFN-a5: NM002169 | HuIFN-a6: NM021002 |
| HuIFN-a7: NM021057 | HuIFN-a8: NM002170 | HuIFN-a10: NM002171 |
| HuIFN-a13: NM006900 | HuIFN-a14: NM002172 | HuIFN-a16: NM002173 |
| HuIFN-a17: NM021268 | HuIFN-a21: NM002175 | HuIFN-a2a: AAS92248 |
| HuIFN-a2b: AAP20099 | HuIFN-a1b: AAL35223 | HuIFN-a4b: CAA26701 |
| HuIFN-aI': AAA52725 (=HuIFN-a17 subtype) | | |
| HuIFN-aI1: CAA01748 (=HuIFN-a17 subtype) | | |
| HuIFN-a-j: CAA23792 | HuIFN-aT: I79343 | HuIFN-aO: I79344 |
| HuIFN-aN: I58999 | HuIFN-aB: 0902162A | |

For example, the preparations of human IFN listed below have also been put to practical use. These are all naturally-occurring IFNα, and they are included in the preferred IFNα of the present invention.

OIF™ brand preparation of IFN (Otsuka Pharmaceutical Co., BALL-1)

Sumiferon™ brand preparation of IFN (Sumitomo Pharma Co., NAMALWA)

Wellferon™ brand preparation of IFN (Glaxo-Wellcome, α-n1)

Alferon™ brand preparation of IFN (Purdue Frederick Co., α-n3)

BALL-1, NAMALWA, α-n1, and α-n3, which are also shown as origins of the above-described naturally-occurring IFNα, are names of cell lines from which the respective IFNα are derived.

"Naturally-occurring" refers to IFNα that is produced by a cell line established from a living body and not prepared by genetic recombination. Naturally-occurring IFNα can be collected from cell culture obtained by culturing cells of the cell lines indicated above as the origins. The methods for culturing cell lines and collecting IFNα from the cultures are known.

Recombinant IFNα is also included in the preferred IFNα of the present invention. Recombinant IFNα refers to IFNα obtained by artificially expressing DNAs encoding the amino acid sequences of IFNα. Furthermore, not only proteins comprising the amino acid sequence of a naturally-occurring IFNα, but also proteins in which the amino acid sequence has been altered can be used as IFNα of the present invention. Specifically, IFNα of the present invention includes, for example, the following proteins:

(a) proteins comprising an amino acid sequence of the naturally-occurring IFNα described above;

(b) proteins comprising an amino acid sequence with substitution, deletion, addition, or insertion of one or multiple amino acid residues in an amino acid sequence of the naturally-occurring IFNα described above, and having the biological activity equivalent to that of the naturally-occurring IFNα;

(c) proteins encoded by a DNA that hybridizes under stringent conditions to the DNA comprising a nucleotide sequence encoding the naturally-occurring IFNα described above, and having the biological activity equivalent to that of the naturally-occurring IFNα; and (d) proteins comprising an amino acid sequence having 90% or higher sequence homology in an amino acid sequence of the naturally-occurring IFNα described above, and having the biological activity equivalent to that of the naturally-occurring IFNα.

Herein, the "biological activity of naturally-occurring IFNα" refers to such activity that when the protein is administered to the oral cavity, the number of causative bacteria of periodontal disease in the cavity is suppressed. Whether a protein has such an activity can be tested by actually administering the protein to the oral cavity of a test animal. Specifically, the number of causative bacteria of periodontal disease can be determined by counting black-pigmented bacteria (BPB), that are grown by inoculating saliva onto *Brucella* HK agar supplemented with 7% defibrinated horse blood and culturing them under an anaerobic condition (70% $N_2$, 15% $H_2$, 15% $CO_2$). When the number of BPB is reduced by administering a protein, the protein is demonstrated to be biologically equivalent to the naturally-occurring IFNα. Whether the number of BPB is reduced is assessed by comparing it with that of a control. For example, the same medium as the one used to dissolve the protein to be tested for activity is administered alone to a group, and the resulting BPB count in this group may be used as control. Alternatively, the number of causative bacteria can also be determined by PCR using primers specific to the bacteria to be counted.

The biological activity can also be compared using the antiviral activity of IFNα as an indicator. In general, the antiviral activity of IFNα is quantitatively assessed by using as an indicator the virus-mediated degeneration of virus-susceptible cells. Such assessment methods include the CPE suppression method described in Example 2. Specifically, the antiviral activity of a test protein is determined by quantitatively assessing the effect of the protein to suppress the degeneration of virus-susceptible cells. The antiviral activity thus determined can be represented, for example, as the reciprocal of the dilution fold of an IFN sample that can suppress 50% cell degeneration.

Herein, the antiviral activity determined by the method described in Example 2 is expressed in "LU" unit. Proteins having, for example, 50% or more, preferably 70% or more, more preferably 80% or more, or even more preferably 90% or more of the antiviral activity as compared with naturally-occurring IFNα are included in the biologically equivalent proteins of the present invention. Alternatively, proteins that are biologically equivalent to naturally-occurring IFNα can be defined as proteins having 80% to 150%, preferably 90% to 120%, or more preferably 95% to 100% of the antiviral activity of naturally-occurring IFNα in the present invention.

Such IFNα with an altered amino acid sequence can be called "IFNα variant (modified form)". There are various known methods for altering given amino acid sequences. The amino acid sequence of IFNα can be altered, for example, by introducing mutations into the nucleotide sequence of an IFNα-encoding polynucleotide. The biological activity can be modulated by altering the amino acid sequence. For example, the biological activity of IFNα can be enhanced or its in vivo stability can be improved. The antigenicity of IFNα can also be altered. Specifically, the antigenicity against heterologous animals can be reduced by altering the amino acid sequence of a heterologous IFNα.

Many methods for altering amino acid sequences are known. Methods described in "Molecular Cloning: A Laboratory Manual" (J. Sambrook, et al., eds., Second Edition, Cold Spring Harbor Laboratory Press, Cold Spring Harbor, N.Y., 1989), "Current Protocols in Molecular Biology" (F. M. Ausubel, et al., eds., John Wiley & Sons, Inc., New York), or other documents can be used, for instance.

Amino acid sequences are altered by substituting, deleting, adding, or inserting amino acid residues. Such substitution, deletion, addition, and insertion of amino acid residues can be done singly, or in combinations of two, three, or all of such modifications. Furthermore, amino acid sequences can be altered by any modifications selected from the group consisting of substitution, deletion, addition, and insertion of amino acid residues at one or multiple positions in the amino acid sequence of naturally-occurring IFNα. Such variants include fusion proteins containing the whole or a partial amino acid sequence of IFNα. There are known methods for predicting the effects of amino acid sequence alterations on protein structure. Thus, variants of IFNα can be designed according to known methods. An example of such methods is described by Dahiyat and Mayo (Science, 1997; 278: 8287). The method of Dahiyat and Mayo can be used to assess whether a structure essential for maintaining the activity remains when the amino acid sequence of IFNα is altered.

Furthermore, it is possible just to alter the amino acid sequence, while the biological activity can be retained. For example, cysteine residues may be substituted or removed to avoid formation of undesired disulfide bonds. Likewise, the protease sensitivity of IFNα can be adjusted by altering the amino acid sequence. Degradation of proteins by proteases in an expression system can be prevented by conferring protease resistance. This allows enhancement of IFNα expression.

When altering the amino acid sequence of IFNα, it is known to be useful to substitute amino acid residues with similar property for retaining the protein structure and activity. Such substitutions of amino acid residues with a similar property are called "conservative substitutions". The "conservative substitutions" refers to amino acid substitutions that do not lead to significant alteration of a protein's tertiary structure and/or activity. For example, substitutions among amino acid residues within each group shown below are included in the conservative substitutions.

(1) neutral hydrophobic side chains (alanine, tryptophan, valine, phenylalanine, proline, methionine, and leucine);
(2) neutral polar side chains (asparagine, glycine, glutamine, cysteine, serine, tyrosine, and threonine);
(3) basic side chains (arginine, histidine, and lysine);
(4) acidic side chains (aspartic acid and glutamic acid);
(5) aliphatic side chains (alanine, isoleucine, glycine, valine, and leucine);
(6) aliphatic hydroxyl side chains (serine and threonine);
(7) amine-containing side chains (asparagine, arginine, glutamine, histidine, and lysine);
(8) aromatic side chain (tyrosine, tryptophan, and phenylalanine); and
(9) sulfur-containing side chain (cysteine and methionine).

Various methods known to those skilled in the art can be used for substitution of amino acids. Specifically, the site-directed mutagenesis of Kunkel et al. (Kunkel, Proc. Nat. Acad. Sci. U.S.A., 1985; 82: 488-492) can be used to substitute amino acids. Alternatively, polynucleotides consisting of the nucleotide sequence encoding a deduced amino acid sequence may be chemically synthesized.

In the present invention, the number of amino acid residues substituted, deleted, added, or inserted is not particularly limited, as long as the resulting variant retains the required biological activity of IFNα. As described above, retention of the biological activity also includes enhancement of the biological activity. The number of amino acid residues to be substituted, deleted, added, or inserted to obtain IFNα variants of the present invention is generally 50 residues or less, for example, 30 residues or less, preferably 20 residues or less, more preferably 10 residues or less, even more preferably 5 residues or less, and still more preferably 1 to 3 residues.

Furthermore, the biological activity of IFNα can be enhanced by altering its amino acid sequence. Species of IFNα with an enhanced biological activity are also included in the IFNα of the present invention. Enhancement of the biological activity includes enhancement of IFNα activity per unit weight, prolongation of retention time in vivo, and suppression of physiological degradation. For example, it has been demonstrated that the biological activity of IFNα can be enhanced by changing the amino acid sequence of IFNα into an amino acid sequence that is conserved among some subtypes (U.S. Pat. No. 4,695,623, U.S. Pat. No. 4,897,471, and U.S. Pat. No. 5,985,265). Such variants can also be used as IFNα of the present invention.

Polynucleotides encoding a variant of IFNα can be obtained through hybridization as well. For example, polynucleotides that hybridize under stringent conditions to a DNA comprising the coding region of a DNA encoding the naturally-occurring IFNα described above are highly likely to encode proteins with the same biological activity as that of IFNα. In the present invention, the "stringent conditions" are specified by parameters known in the technical field. Specifically, conditions of DNA hybridization where the ionic strength is low and the temperature is slightly below the melting temperature (Tm) of DNA hybrid complex are generally defined as stringent conditions. Specifically, conditions where the temperature is about 3° C. lower than Tm are included in the stringent conditions. As the stringency gets higher, the degree of homology between probe and target sequence becomes higher.

For further information on such conditions, one may refer to references summarizing similar methods. Specifically, such methods are described in, for example, "Molecular Cloning: A Laboratory Manual" and "Current Protocols in Molecular Biology" indicated above. By such methods, a DNA encoding the above-described naturally-occurring IFNα can be used as a probe to screen a cDNA library of a species from which IFNα has not been isolated, and isolate IFNα-encoding cDNAs from that species. Alternatively, there is a possibility that novel subtypes of IFNα can be isolated from a cDNA library of a species from which IFNα has already been isolated.

The stringent conditions include, for example, hybridization at 65° C. using 6×SSC. The stringent conditions also include hybridization at 65° C. using a hybridization buffer containing 3.5×SSC, 0.02% Ficoll, 0.02% polyvinylpyrrolidone, 0.02% bovine serum albumin, 2.5 mM $NaH_2PO_4$ (pH 7), 0.5% SDS, and 2 mM EDTA. SSC contains 0.15 M sodium chloride and 0.15 M sodium citrate (pH 7). In the stringent conditions, the DNA-transferred membrane is washed using 2×SSC at room temperature after hybridization, and then washed using 0.1×SSC/0.1×SDS at a temperature up to 68° C.

Alternatively, formamide hybridization solutions may be used instead of an aqueous hybridization solution. Specifically, the stringent hybridization conditions can be achieved, for example, by using 50% formamide solution at 42° C. Those skilled in the art can use other conditions and reagents to achieve comparable stringency. Furthermore, methods of screening cells and libraries for the purpose of expressing variants, methods for isolating such variants, and methods for cloning and sequencing DNAs of interest are also known. For example, primers for amplifying DNAs can be designed based on the nucleotide sequences of the DNAs to be isolated. The DNAs of interest can be amplified by gene amplification methods such as PCR using primers.

In the present invention, the amino acid sequence homology between naturally-occurring IFNα and its variant is in general at least 65%, typically 75%, preferably 90%, more preferably 95% or higher, and still more preferably 99% or higher. The amino acid sequence homology can be calculated using various software tools developed and disclosed by NCBI (Bethesda, Md.). Analytical tools for nucleotide and amino acid sequences include the heuristic algorithm of Altschul S. F., et al. (J. Mol. Biol., 1990; 215: 403-410). This tool is known as BLAST.

In the present invention, IFNα may be modified with other molecules as long as it retains its biological activity. Specifically, fusion proteins between IFNα and other proteins may be used as IFNα of the present invention. Furthermore, IFNα may be modified with non-protein polymers. For example, IFNα modified with polymers such as polyethylene glycol has been used as a preparation administered into the blood (U.S. Pat. No. 5,382,657, U.S. Pat. No. 5,559,213, U.S. Pat. No. 6,177,074, U.S. Pat. No. 5,951,974, and U.S. Pat. No. 5,981,709). Such modifications with polymers can improve the retention of IFNα in the blood.

IFNα used in the present invention can be synthesized chemically or by genetic engineering based on its amino acid sequence. Alternatively, naturally-occurring IFNα may be used in the present invention. Naturally-occurring IFNα can be extracted from organisms or biological materials. Alternatively, naturally-occurring IFNα can also be collected from cultures obtained by culturing IFNα-producing cells. Of such methods, the synthesis method by genetic engineering is a preferred method for obtaining homogeneous IFNα on a large scale easily. When the amino acid sequences to be synthesized are known, those skilled in the art can predict the encoding nucleotide sequences and synthesize them. Alternatively, those skilled in the art can prepare cDNA for naturally-occurring IFNα or its variants and translate them into proteins. There are many known methods of in vivo or in vitro protein translation based on amino acid sequence-encoding DNAs. For example, to translate proteins in vivo, in general, 5'-untranscribed and 5'-untranslated sequences, which are involved in transcription and translation initiations, respectively, and the like can be combined, if required. More specifically, a promoter sequence for regulating gene transcription can be linked to a gene as a 5'-untranscribed regulatory sequence. An enhancer can also be added as a transcribed regulatory sequence.

Expression vectors containing all the elements necessary for expression are available on the market. Known vectors are also described, for example, in "Molecular Cloning: A Laboratory Manual" (Sambrook, et al., Second Edition, Cold Spring Harbor Laboratory Press, 1989). In general, such commercially available vectors are equipped with multi-cloning sites for inserting amino acid sequence-encoding DNAs. Expression vectors can be prepared by digesting the DNA to be expressed with appropriate restriction enzymes and inserting it into a cloning site. Restriction enzyme sites that are needed can also be prepared by ligation with synthetic oligonucleotides. IFNα can be expressed as a fusion protein by using fusion protein-expression vectors. For example, vectors that can be attached with a myc or His tag or such are also known.

The expression vectors thus prepared are introduced into and transform host cells that allow translation of proteins of interest. Such host cells include, for example, the following cells:

prokaryotic cells (for example, *E. coli*); and
eukaryotic cells (for example, CHO cell, COS cell, yeast expression system, and insect cells).

When the IFNα to be used in the present invention is predicted to contain glycosylation sites, eukaryotic cells are preferably used as host cells. For example, at least three glycosylation sites are predicted in the amino acid sequence of canine IFNα shown in SEQ ID NO: 4 (FIG. 1). Thus, eukaryotic cells can be used to express the canine IFNα of SEQ ID NO: 4.

The eukaryotic cell expression systems include, for example, insect cells. Methods for expressing foreign DNAs in insect cells using the baculovirus expression system are known. Foreign DNAs can be expressed in insect cells, for example, by the method described in the Examples.

Since naturally-occurring IFNα is secretory proteins, signal sequences are generally encoded in the IFNα-encoding cDNAs derived from a living body. For example, the N-terminal 23 residues of the canine IFNα shown in SEQ ID NO: 3 correspond to a signal sequence. This is supported, for example, by the fact that the expression product in insect cells contains a protein with a molecular weight corresponding to the mature protein.

When the IFNα to be used in the present invention is synthesized by genetic engineering techniques as described above, a foreign signal sequence may be used as the signal sequence. For example, when human IFNα is expressed in nonhuman cells, a functional signal sequence in the species from which the cells used for the actual expression have been derived can be used. In this case, a chimeric protein is expressed, in which a signal sequence that is functional in the nonhuman species is attached to the amino acid sequence of a mature human IFNα protein. The signal sequence is removed during the process of secretion of the expressed recombinant protein to the outside of cells. As a result, the mature human protein is secreted. Alternatively, when it is not necessary to secrete the protein to the extracellular space, a DNA encoding the amino acid sequence of the mature protein can also be expressed. When the deletion of the signal sequence results in loss of the start codon, a start codon (atg) can be artificially added to the 5' end.

When the amino acid sequence containing a signal sequence is expressed, IFNα is accumulated in the culture supernatant. Alternatively, when the amino acid sequence does not have a signal sequence and is expressed, the mature IFNα protein is accumulated in the cells. After collection and purification from the culture, such IFNα expressed by gene recombination can be used for the compositions of the present invention. Methods for collecting and purifying IFNα from cultures are known. Alternatively, cultures containing the expression product or crude preparation can be used for the compositions of the present invention. For example, IFNα expressed using yeast as the host can be freeze-dried without removing the yeast cells, and formulated into the compositions of the present invention.

Alternatively, the IFNα to be formulated into the oral compositions of the present invention may be expressed using a plant as host. In this case, plants or plant cells of a transformed plant that express IFNα can be used as raw materials for the oral compositions of the present invention. Specifically, the present invention provides compositions for oral administration to prevent and/or treat periodontal disease, comprising a transformed plant containing an IFNα-encoding gene in an expressible manner. Furthermore, the present invention relates to compositions for oral administration to prevent and/or treat periodontal disease, comprising an IFNα-containing fraction derived from a transformed plant containing an IFNα-encoding gene in an expressible manner.

For example, IFNα-containing tissues of a transformed plant may be destroyed and formulated into oral compositions of the present invention. Such plant tissues can be crushed after drying. Alternatively, crushed plant tissues may be dried. Alternatively, IFNα-containing tissues of a transformed plant are homogenized, and filtered if required, and the resulting IFNα-containing solution can be formulated into the oral compositions of the present invention without further treatment or after being dried. Such IFNα-containing fractions derived from transformed plants are all included in the "transformed plants" of the present invention.

The oral compositions of the present invention can be produced without making significant changes in current manufacturing processes, by using the same plants as currently used as materials for feed or pet food as transformed plants.

Specifically, such plants include potato, tomato, beans, cereals, fruits such as strawberry, and pasture grasses. Beans include soybeans and azuki-beans. Cereals may include rice plant, wheat, and corn.

The transformed plant cells used in the present invention can be prepared by introducing a vector carrying an IFNα-encoding gene (or a protein having a biological activity equivalent to IFNα) into plant cells, and expressing the gene. When IFNα is expressed in plant cells, an endoplasmic reticulum retention signal may be attached to the C terminus of IFNα. The endoplasmic reticulum retention signal consists of an amino acid sequence shown below, for example. Secretory proteins with an endoplasmic reticulum retention signal are stably maintained in the endoplasmic reticulum after expression.

```
KDEL (Lys-Asp-Glu-Leu)/    SEQ ID NO: 7
RDEL (Arg-Asp-Glu-Leu)/    SEQ ID NO: 8
```

Specifically, the present invention provides oral compositions for preventing and/or treating periodontal disease, which comprise a transformed plant carrying in an expressible manner an IFNα-encoding gene with an endoplasmic reticulum retention signal attached to its C terminus. Furthermore, the present invention relates to oral compositions for preventing and/or treating the periodontal disease, which comprise a fraction containing IFNα derived from a transformed plant carrying in an expressible manner an IFNα-encoding gene with an endoplasmic reticulum retention signal attached to its C terminus.

Vectors used for gene expression in plant cells are not particularly limited, as long as they contain a promoter that allows transcription in the plant cells and a terminator sequence containing a polyadenylation site required for the stabilization of transcripts. Vectors that can be used include, for example, the "pBI121", "pBI221", and "pBI101" plasmids (all from Clontech). The promoters that allow transcription in plant cells include, for example, promoters that allow constitutive gene expression in plant cells and promoters that are inducibly activated upon foreign stimulation. Known promoters that allow constitutive expression include the following promoters:

cauliflower mosaic virus 35S promoter (Odell et al., Nature, 1985; 313: 810);

rice plant actin promoter (Zhang et al., Plant Cell, 1991; 3: 1155); and maize ubiquitin promoter (Cornejo et al., Plant Mol. Biol., 1993; 23: 567).

IFNα can be expressed in plant cells by introducing plant cells with a vector carrying an IFNα-encoding gene operably linked to such a promoter. Herein, "operably linked" means that a promoter is linked to an IFNα-encoding gene so that IFNα is expressed in plant cells. "Plant cells" to be transformed include various types of plant cells. Transformants can be prepared by introducing vectors into, for example, suspension culture cells, protoplasts, leaf pieces, or calluses.

Methods for introducing vectors into such plant cells are known. Specifically, various methods known to those skilled in the art can be used, including *Agrobacterium*-mediated methods, polyethylene glycol methods, electroporation, and particle gun methods.

Plants can be regenerated by re-differentiating the transformed plant cells. Re-differentiation methods, which vary depending on the plant species, have already been established. Methods for re-differentiating each plant species are listed below.

Potato:
Method of Visser et al. (Theor. Appl. Genet, 1989, 78: 594); Tuber disc methods.

Monocotyledonous Cereals Such as Rice Plant:
Method of Hiei et al. (Hiei, Y., Komari, T., Kubo, T. Transformation of rice mediated by *Agrobacterium tumefaciens*. Plant Mol. Biol., 1997; 35: 1-2 205-18);
Method of Ishida et al. (Ishida, Y., Saito, H., Ohta, S., Hiei, Y., Komari T., Kumashiro T. High efficiency transformation of maize (*Zea mays* L.) mediated by *Agrobacterium tumefaciens*. Nat. Biotechnol., 1996 June; 14: 6 745-50);

Electroporation (Shimamoto, K., Terada, R., Izawa, T. et al. Fertile transgenic rice plants regenerated from transformed protoplasts. Nature, 1989; 338: 274-276); etc.

Strawberry:

Method of Asao et al. (Asao, H., Y. Nishizawa, S. Arai, T. Sato, M. Hirai, K. Yoshida, A. Shinmyo and T. Hibi. Enhanced resistance against a fungal pathogen *Sphaerotheca humuli* in transgenic strawberry expressing a rice chitinase gene. Plant Biotechnology, 1997; 14(3): 145-149).

Once a transformed plant with an IFNα-encoding gene introduced into its genome (chromosome) is generated, progeny can be obtained from the plant via sexual or asexual reproduction. Alternatively, the plant can be produced on a large scale from breeding materials obtained from the plant and its progeny, or their clones. The breeding materials include, for example, seeds, fruits, cut panicles, tubers, tuberous roots, strains, calluses, and protoplasts.

Furthermore, techniques using plant virus vectors for expressing proteins of interest in plants are known. When plant virus vectors that do not integrate into the genome are used, foreign genes are generally not transferred to progeny. So far, however, the expression level of a foreign gene expressed using a plant virus vector is known to be higher than that achieved by a chromosome integration method such as the *Agrobacterium*-mediated method. The tobacco mosaic virus vector is a known practicable plant virus vector. Specifically, substances of interest can be produced in plants by growing the plants and inoculating them with infectious RNA transcribed from a constructed expression gene during the inoculable period.

The compositions of the present invention are useful in preventing and/or treating the mammalian periodontal diseases. Herein, prevention refers to suppressing the progression of periodontal disease symptoms. In cases where no such symptoms manifest, prevention means delaying the onset of symptoms. The treatment of periodontal disease refers to the alleviation of at least one of periodontal disease symptoms. In the present invention, periodontal disease symptoms to be prevented or treated include gingival swelling, pain, and bleeding. These symptoms are caused by gingival inflammation. Thus, gingival inflammation is also included in the periodontal disease symptoms.

Furthermore, since periodontal disease is produced by specific oral bacteria, suppression of the number of these pathogenic bacteria is also included in the prevention or treatment. In the present invention, the causative bacteria of periodontal disease include black-pigmented Gram-negative anaerobic bacteria. The presence of such microorganisms can be confirmed, for example, by testing whether black-pigmented bacteria are grown under an anaerobic condition on *Brucella* HK agar supplemented with defibrinated horse blood. Specifically, microorganisms of the genera *Porphyromonas* and *Prevotella* are known as causative bacteria of periodontal disease. The most frequently isolated bacterial species is *P. gingivalis*. In addition, *P. endodontalis*, *P. circumdentaria*, *P. canons*, *P. salivosa* and such are also often isolated.

A preferred mammal to which the compositions of the present invention are administered is human. In addition, pet animals such as dogs and cats, and mammals bred in zoos are also preferred as mammals in the present invention. Such mammals include pigs, boars, goats, sheep, horses, cattle, deer, donkeys, reindeer, rabbits, monkeys, gorillas, orangutans, chimpanzees, bradypods, elephants, giraffes, rhinoceroses, hippopotamuses, tapirs, wolves, hyenas, bears, pandas, lesser pandas, masked palm civets, foxes, raccoon dogs, raccoons, tigers, lions, leopards, cheetahs, otters, seals, fur seals, Steller's sea lions, sea lions, dolphins, killer whales, and whales.

In the present invention, "oral compositions" refers to compositions which are to be administered into the oral cavity of a mammal. The oral compositions of the present invention can be produced by combining interferon α with biologically acceptable carriers. The biologically acceptable carriers include carriers that are inactive to the interferon α to be formulated and inactive in organisms to which the compositions are to be administered. "Carriers that are inactive in organisms" refers to carriers that do not interfere with normal functions in organisms. Such normal functions in organisms include metabolic functions, reproductive functions, motor functions, and neural functions. For example, ingredients that are metabolized through normal metabolic functions in organisms are included in the biologically acceptable carriers. Furthermore, ingredients that are hardly or not at all digested or metabolized and which do not interfere with biological functions are all included in the biologically acceptable carriers.

For example, food formulated with IFNα is a preferred embodiment of the oral compositions of the present invention. The compositions of the present invention can be administered into the oral cavity as food as well as by applying or spraying them onto oral tissues. The compositions of the present invention can also be administered as a pharmaceutical composition for preventing or treating periodontal disease.

Specifically, the present invention relates to pharmaceutical compositions for preventing and/or treating periodontal disease, which comprise interferon α as an active ingredient. The present invention also relates to pharmaceutical compositions for preventing and/or treating periodontal disease, which comprise interferon α and pharmaceutically acceptable carriers. Furthermore, the present invention relates to the use of interferon α in producing pharmaceutical compositions for preventing and/or treating periodontal disease. The present invention also relates to the use of interferon α in methods for preventing and/or treating periodontal disease.

In particular, there was no method known for actively treating periodontal disease in prior art. As described in the Examples, it was confirmed by the present invention that administration of the therapeutic agent of the present invention for periodontal disease produces a therapeutic effect on advanced periodontal disease. Specifically, the present invention provides therapeutic agents for periodontal disease, which comprise interferon α as an active ingredient. Furthermore, the present invention relates to pharmaceutical compositions for treating periodontal disease, which comprise interferon α and pharmaceutically acceptable carriers. In addition, the present invention relates to the use of interferon α in producing pharmaceutical compositions for treating periodontal disease. Furthermore, the present invention relates to the use of interferon α in treating periodontal disease.

Next, specific embodiments of oral compositions of the present invention, which comprise interferon α, are described below.

Food Compositions Containing Interferon α:

In general, compositions of the present invention can be prepared by formulating interferon α into an ingredient ingested as food or feed for mammals. In particular, when feed is given to pet animals, it is called pet food. Pet food is included in the food or feed of the present invention. "Pet animals" refers to nonhuman animals bred for ornamental and sporting purposes. Animals bred, for example, as working animals or for animal products such as meat, eggs, hair, milk, and such are in general included in farm animals, and distinguished from pet animals. However, some animals bred to perform specific tasks (working animals) such as police dogs and guide dogs may consume the same type of feed as sporting animals. Even if some animals are bred as working animals, as long as they are of the same species as pet animals and consume the same type of feed as pet animals, their feed is included in the pet food defined in the present invention.

In general, food and feed contain carbohydrates, proteins, minerals, fats, water, fibers, and the like, and most of the materials are animal or plant tissues, microorganism cells, and their processed products. "Processed products" refers to products yielded from such materials via some processes such as heating, drying, freeze-drying, and extraction. A series of processes for obtaining a processed product may contain a combination of several different steps.

Food and feed may be formulated with preservatives, antiseptic agents, antioxidants, dyes, flavors, humectants, seasonings, and such. Components such as expanders, binders, and viscosity adjusters can be added depending on the type of food, and naturally-occurring or synthetic components are used. Food compositions of the present invention can be produced by formulating IFNα into materials commonly used for food or feed. Alternatively, oral compositions of the present invention can be prepared by adding IFNα to IFNα-free food or feed at the time of ingestion. Next, specific examples of the oral compositions of the present invention are described below.

Food or feed compositions of the present invention can be prepared by adding interferon α to materials generally used as food or feed. The amount of interferon α added to prepare the food or feed compositions of the present invention is typically 0.1 to 1,500 LU/day/kg body weight, preferably 0.05 to 2,500 LU/day/kg body weight. In other words, interferon α can be formulated at 0.1 to 1,500 LU/kg body weight, preferably 0.05 to 2,500 LU/kg body weight to a standard daily amount of food or feed to be ingested. When the food composition is a nonessential food such as chewing gum, the dosage of interferon α can be controlled by indicating the daily amount of the food to be ingested according to its blending quantity of interferon. For example, when the blending quantity in a single piece of chewing gum corresponds to the daily dose, the recommended amount of the chewing gum to be ingested is a single piece per day.

Chewable Compositions Containing Interferon α:

The IFNα-containing compositions of the present invention can be prepared as chewable oral compositions by combining IFNα with chewable carriers. Specifically, the present invention provides oral compositions containing IFNα and chewable carriers. Herein, "chewable carrier" refers to components that are masticated when administered to the oral cavity of an animal. Such chewable carriers may be materials that are hard to crush or materials that can be crushed into pieces by mastication.

Specifically, chewable carriers include, for example, glucose, sucrose, maltose, sorbitol, xylitol, trehalose, starch, gelatin, alginic acid, alginate, cellulose, ethylcellulose, carboxymethylcellulose, hydroxypropylcellulose, hydroxypropylmethylcellulose, guar gum (polygalactomannan), glucomannan, xanthan gum, and Carbopol.

Furthermore, various gum bases are also included in the chewable carriers of the present invention. Carriers whose volumes remain constant even after being chewed for a long time in the mouth are in general used as gum bases. Gum bases include, for example, plant resins, chicle, vinyl acetate resins, ester gum, polyisobutylene, calcium carbonate, and jelutong (Pontianak). When the chewable composition of the present invention is processed as an oral composition for human, gum bases are particularly preferred as chewable carriers.

When the chewable compositions of the present invention are used as pharmaceuticals, they are chewable pharmaceutical compositions. When the chewable compositions of the present invention are provided as food, they are chewable food. When the compositions of the present invention are used as chewable feed, they are chewable feed compositions. The size of a chewable composition can be adjusted to induce mastication in nonhuman animals. Specifically, mastication can be induced in nonhuman animals by processing the compositions to be bulkier than an easy-to-swallow size. More frequent mastication can also be induced by increasing the hardness depending on the type of animal.

Paste-Type Compositions Containing Interferon α:

The IFNα-containing compositions of the present invention can also be prepared as paste-type oral compositions by combining IFNα with paste carriers. Specifically, the present invention provides oral compositions containing IFNα and paste carriers. Herein, the paste carrier may also be referred to as a carrier with semisolid consistency. Furthermore, the paste carriers also include gel carriers.

Paste-type compositions can be prepared, for example, by adding a solvent such as water to water-soluble polysaccharides or polymers. The water-soluble polysaccharides and polymers include glucose, sucrose, maltose, sorbitol, xylitol, starch, gelatin, pectin, alginic acid, alginate, cellulose, ethylcellulose, carboxymethylcellulose, hydroxypropylcellulose, hydroxypropylmethylcellulose, guar gum (polygalactomannan), glucomannan, carrageenan, xanthan gum, tamarind gum, Carbopol, agarose, and agar. In addition to these, polymers such as polyethylene glycol and polyvinylpyrrolidone can be formulated as gel carriers into the compositions of the present invention.

The paste- or gel-type compositions of the present invention can be administered, for example, by applying them on oral tissues. The oral tissues include gingiva, teeth, sublingual tissues, buccal cavity, buccal mucosa, and such. It is preferable to apply a composition on gingiva because this enables direct administration of the composition to lesions of periodontal disease. Alternatively, a preferred administration method is to apply a composition on buccal cavity. Application of paste-type compositions on oral tissues is an administration method that can also be applied to nonhuman animals. Compositions of the present invention can also be administered as tooth paste, which is applicable primarily in human. Specifically, tooth paste formulated with IFNα is used as a composition of the present invention. Needless to say, the compositions of the present invention can be administered in the form of tooth paste to animals that accept toothbrushing.

Compositions of the present invention can be in any form of choice such as solid, gel, or liquid. In order to maintain IFNα activity, the compositions are preferably in a dried form when they are distributed on the market. The dried compositions can be converted into gel or liquid by adding an appropriate solvent such as water to the compositions at the time of ingestion. The compositions of the present invention may also be distributed on the market in a freeze-dried form.

Compositions of the present invention may contain additional components such as flavors, dyes, corrigents, sweeteners, and seasonings. Known components that are known to have a preventive or therapeutic effect on periodontal disease can also be combined with the compositions of the present invention. The toothbrushing effect can also be achieved by further formulating plant fibers or such into compositions formulated with chewable carriers.

The content of IFNα formulated into oral compositions of the present invention is usually 0.05 to 2,500 LU/day/kg body weight, for example, 0.1 to 1,500 LU/day/kg body weight, more specifically 0.2 to 500 LU/day/kg body weight, typically 0.2 to 50 U/day/kg body weight, and preferably about 0.2 to 1 LU/day/kg body weight. To achieve an antiviral effect, IFNα is administered to the blood stream at a very high dose such as several to 10 MIU. By contrast, in the present invention, the objective can be achieved at a low dose. In the present invention, the risk of side effect produced by the administration of IFNα is reduced to a negligibly low level by keeping the quantity of IFNα used low. The blending ratio of IFNα in a composition of the present invention can be determined based on the amount of the composition to be ingested. For example, the amount of IFNα added to feed can be determined based on the daily amount of feed to be ingested and the body weight of the animal to which a composition of the present invention is to be administered.

One LU in the present invention corresponds to 1 IU of naturally-occurring human IFNα. In general, cells that are responsive to the IFNα-like activity of a test protein are used to assess its antiviral effect. Thus, canine cells are used in Example 2. The antiviral effect of human IFNα is generally assessed by using human cells. It is thus difficult to directly compare their activities. However, since the principle of measuring antiviral activity is common to both, 1 LU can be assumed to be equivalent to 1 IU.

Alternatively, instructions can be given to explain that the daily amount (g) of oral composition of the present invention to be ingested per kilogram of body weight is based on the blending quantity of IFNα in the composition. Specifically, the present invention provides kits for preventing and/or treating periodontal disease, which comprise (1) an oral composition comprising interferon α and biologically acceptable carriers; and (2) instructions describing the effective dose of the composition to prevent and/or treat periodontal disease.

In the present invention, the titer (LU) of IFNα is determined by the following procedure.

A serial dilution is prepared for the protein of which titer should be determined. The antiviral activity at each dilution is assessed, for example, by the CPE suppression method (J. Vet. Med. Sci., 1996; 58(1): 23-27). Specifically, as described in Example 2, vesicular stomatitis virus (VSV) can be used as virus and the canine A-72 cell (ATCC CRL-1542) can be used as virus-susceptible cell. The degeneration of A-72 cells can be quantitatively assessed by crystal violet staining. The antiviral activity (LU) is defined as the reciprocal of the dilution at which an IFN sample can suppress 50% of VSV-mediated A-72 cell degeneration.

When administered into the oral cavity of an animal, the oral compositions of the present invention can achieve the effect of preventing and/or treating periodontal disease. Specifically, the present invention provides methods for preventing and/or treating periodontal disease in mammals, which comprise the step of administering interferon α into the oral cavity. In particular, methods for treating periodontal disease, which comprise the step of administering interferon α into the oral cavity of a human or nonhuman animal, are a preferred embodiment of the present invention.

Compositions of the present invention can be administered into the oral cavity of a mammal in any form such as solid, paste, gel, or liquid. Solid preparations can be administered via chewing or swallowing. Solid preparations can also be administered into the oral cavity in the form of lozenge (so-called troche). Paste- or gel-type preparations can be administered by chewing or swallowing, or by applying them on oral tissues. Liquid preparations can be administered by swallowing, as well as by gargling or mouth washing, or by spraying them into the oral cavity.

When the oral compositions of the present invention are administered as a medical treatment, they are used as pharmaceutical compositions. Specifically, the present invention provides pharmaceutical oral compositions for preventing and/or treating periodontal disease in mammals, which comprise interferon α and pharmaceutically acceptable carriers. The pharmaceutically acceptable carriers that can be used in the present invention may be inactive carriers that are generally used in formulating pharmaceutical preparations.

Hereinbelow, the present invention is specifically described with reference to the Examples.

All prior art documents cited herein are incorporated herein by reference.

EXAMPLES

Example 1

Preparations of Canine IFNα4 Expressed with Baculovirus (BacCaIFNα4)

The CaIFNα gene was amplified from a canine cell-derived cDNA library by PCR using primers consisting of the nucleotide sequences shown below. The cDNA library was prepared using as a template mRNA of MDCK cells stimulated by ultraviolet-inactivated Newcastle-disease-virus strain B1.

```
Sense primer (SEQ ID NO: 5):
5'-gcaggatccacgATGGCCCTGC-3'
(Lowercase ggatcc is the BamHI sequence)

Antisense primer (SEQ ID NO: 6):
5'-gctggatccgtca[atgatgatgatgatgatgatg]TTTCCTCCT
CCTTACTCTTC-3'
```

(Lowercase ggatcc is the BamHI sequence; the sequence in the parentheses is a nucleotide sequence encoding His-Tag)

The fragment obtained by PCR amplification was cloned into the pCR2.1 vector by TA cloning. *E. coli* cells were transformed with the construct. The transformants were grown, and the plasmids were prepared from the bacterial cells. The nucleotide sequence of the inserted cDNA in the plasmids was confirmed. The confirmed nucleotide sequence of the inserted fragment and the encoded amino acid sequence are shown in FIG. 1. After the nucleotide sequence was confirmed, the BamHI fragment in the plasmid was recloned into the baculovirus transfer vector pAcYM1 (J. Gen. Virol., 1987; 68: p 1233-1250). Recombinant viruses were prepared through cotransfection. The resulting recombinant viruses were inoculated to insect cell Sf9. The expression products were collected and purified by the Ni column method. About 0.2 mg/ml of BacCaIFNα4 was yielded.

Purified BacCaIFNα4 was separated by SDS-PAGE and stained with CBB. As a result, three bands of about 27, 25, and 23 kDa were detected (FIG. 2A). Western blotting was conducted using a rabbit anti-BacCaIFNα4 serum antibody (primary antibody) obtained by immunization using purified BacCaIFNα4, and a horse radish peroxidase (HRP)-labeled goat anti-rabbit IgG serum antibody (secondary antibody). As a result, bands with sizes corresponding to the three detected by CBB staining were detected. The molecular weights of Pre BacCaIFNα4 and mature BacCaIFNα4 which lacks the signal peptide region (FIG. 1, solid-line boxed region in the amino acid sequence) deduced from the nucleotide sequence were 22.2 and 19.8 kDa, respectively. Purified IFN protein expressed by the baculovirus expression system has been known to contain several IFN protein species of interest due to the presence of pre and mature forms and differences in the number of attached sugar chains (three glycosylation sites are indicated by double underline in the amino acid sequence of FIG. 1). Although no detailed examination has been carried out to date, the three major bands of BacCaIFNα4 detected in CBB staining and Western blotting are also assumed to result from the same phenomenon described above.

Example 2

Assessment of the Biological Activity of BacCaIFNα4

The purified BacCaIFNα4 sample prepared as described in Example 1 was serial-diluted, and the antiviral activity was determined by the CPE suppression method (J. Vet. Med. Sci., 1996; 58(1): 23-27) (FIG. 2B). The virus and susceptible cell used were vesicular stomatitis virus (VSV) and canine A-72 cell (ATCC CRL-1542), respectively. Specifically, A72 cells were suspended in a growth medium and plated in 96-well plates at $1 \times 10^4$/well. The cells were cultured in a $CO_2$ incubator at 37° C. for two days. The composition of the medium used in the Examples is as follows.

Maintenance medium: Eagle MEM supplemented with L-glutamine and $NaHCO_3$

Growth medium: maintenance medium supplemented with 5% FCS (final concentration)

Two days later, IFNα solutions were subjected to 4-fold serial dilution with maintenance medium starting from 16.000-fold dilution, and 100 μl each of the diluted solutions was added to a sample well. The maintenance medium alone was added to control-virus wells. The cells were cultured in a $CO_2$ incubator at 37° C. for one day. VSV was adjusted to 100 $TCID_{50}$/ml and inoculated to the sample and control-virus wells (10 μl per well). The maintenance medium alone (10 μl) was added to each noninfected-control well. The cells were cultured in a $CO_2$ incubator at 37° C. for three days. Three days after addition of IFNα, 80 μl of 0.5% crystal violet staining solution was added to each well, and the cells were allowed to stand under UV irradiation for 30 minutes. After washing with running water and air-drying, the absorbance (570 nm) of each well was measured in a plate reader. The antiviral activity was defined as the reciprocal of the dilution of an IFN sample that can suppress 50% of VSV-mediated A-72 cell degeneration. The dilution of an IFN sample that can suppress 50% of cell degeneration was determined by the procedure described below.

Assume the absorbances of control-virus and noninfected-control wells at 570 nm were A and B, respectively. The value of (A+B)/2 was taken as the absorbance at 570 nm in the state of 50% cell degeneration. The dilution fold which corresponds to that absorbance was determined from the graph. Since the absorbances of control-virus and noninfected-control wells were 0.21 and 1.168, respectively, (0.21+1.168)/2=0.689 was assumed to be the absorbance in the state of 50% cell degeneration. From the graph, the antiviral activity of the BacCaIFNα4 sample was determined to be $1,024 \times 10^4$ LU/ml (specific activity was $5 \times 10^4$ LU/μg).

Example 3

Administration Experiment (1)

A very low dose of BacCaIFNα4 was orally administered to beagles. The laboratory dogs used were five beagles (eight to nine months old, female, 9 to 10 kg body weight). The dose was 2.5 LU per dog. The preparation was a maltose paste and it was applied on sublingual tissues. The preparation was prepared by combining 1 g of maltose with 390 μl of sterile distilled water and adding 10 μl of BacCaIFNα4 (2,500 LU/ml). The preparation was administered for five consecutive days. The animals were examined two, five, and eight days after administration. Before BacCaIFNα4 administration, a mixture of 400 μl of sterile distilled water and 1 g of maltose was administered to an experimental group as a control group. The animals were examined two, five, eight, and twelve days after administration. The animals were tested for occult blood which serves as an indication for potential progression of inflammation. The occult blood test was carried out by examining collected saliva using the test paper for salivary examination "Salivaster" (Showa Yakuhin Kako Co., trade name).

Figure 3:
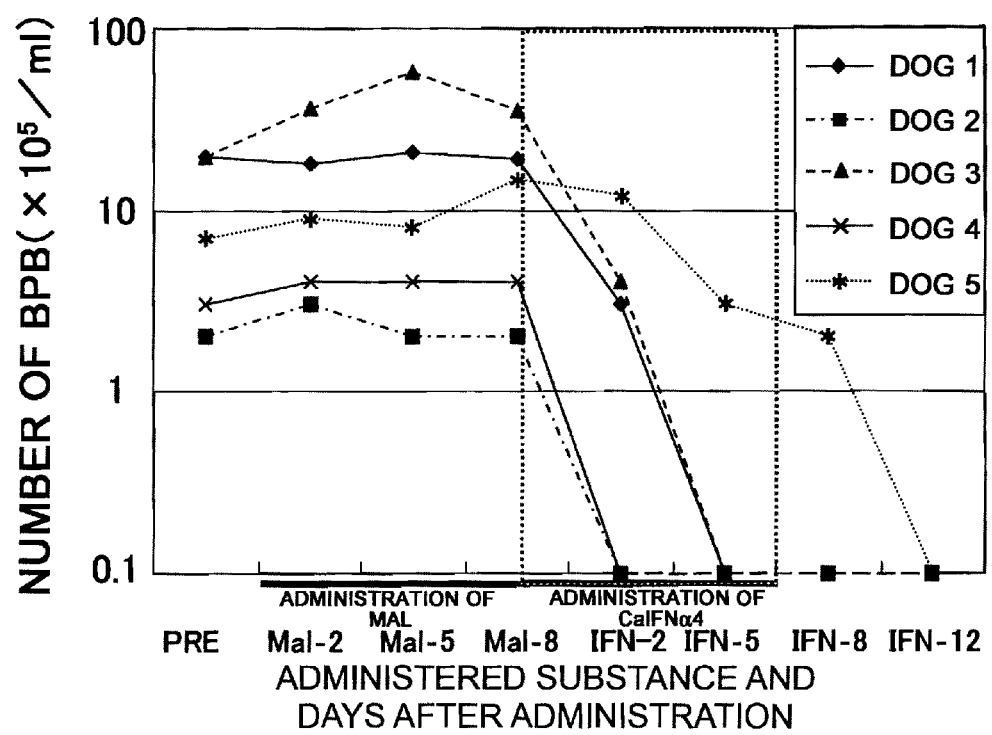
FIG. 3 is a graph showing the number of black-pigmented bacteria (BPB) in dogs of Administration experiment (1). In this graph, the vertical axis indicates the number of salivary BPB ($\times 10^5$/ml) and the horizontal axis indicates the duration of administration (day) of a therapeutic agent of the present invention or control. In this graph, for example, "IFN-2" indicates the result obtained two days after IFNα administration; "PRE" indicates the result obtained on day 0; and "Mal-8" indicates the result obtained eight days after administration of a control (maltose). Each plot was obtained from the result for the five dogs tested.

Saliva (10 μl) was collected and serial-diluted with the BHI liquid medium. Its 10-μl aliquots were inoculated on Brucella HK agar plates supplemented with 7% defibrinated horse blood. The plates were incubated for five days under an anaerobic condition (70% $N_2$, 15% $H_2$, 15% $CO_2$). The number of causative black-pigmented bacteria (BPB) of periodontal disease as well as the total number of anaerobic bacteria was determined. None of the symptoms suggesting gingivitis was detectable in any dog before the start of experiment (Pre), in the maltose administration group (Mal), and in IFN administration group (IFN). As shown in FIG. 3, the number of BPB was significantly reduced in the IFN administration group. By contrast, the number was constant or increased in the Mal group.

Figure 4:
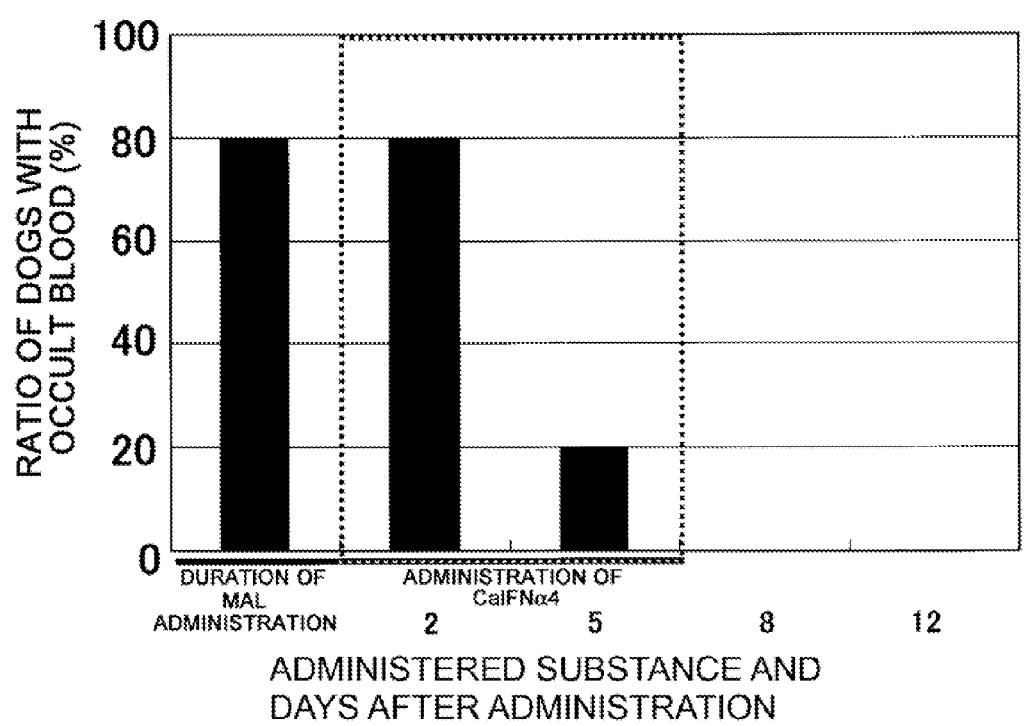
FIG. 4 is a diagram showing the salivary occult blood reaction in dogs of Administration experiment (1). In this diagram, the vertical axis indicates the ratio of dogs in which the occult blood reaction was detected, and the horizontal axis indicates the duration of IFNα administration (two to twelve days). The result of Mal administration is shown as the ratio of dogs in which the occult blood reaction was detected when Mal was administered prior to IFNα administration.

As shown in FIG. 4, salivary occult blood was found in four-fifths (80%) of the dogs in the Mal group. Two days after IFN administration, the frequency and level of salivary occult blood were found to be comparable in these dogs; however, the frequency was reduced to one-fifths (20%) five days after IFN administration. Eight and twelve days after IFN administration, salivary occult blood was not detectable in any dog. These results suggest that oral administration of a very low dose of BacCaIFNα4 produced the effect of suppressing causative bacteria of periodontal disease and suppressed early gingival inflammation.

Example 4

Administration Experiment (2)

A very low dose of BacCaIFNα4 was orally administered to beagles (female, 15 months old, 9 to 13 kg body weight) affected with gingivitis. The dose was 0.25 LU/kg body weight. A maltose paste was prepared to contain the indicated dose of BacCaIFNα4 and applied once a day on canine oral tissues, in particular, buccal gingivae, after feeding the dogs continuously for seven days. The preparation was prepared by combining 790 μl of sterile distilled water with 2 g of maltose, and adding 10 μl of BacCaIFNα4 (5,000 LU/ml). The maltose paste (14 mg) contained 0.25 LU BacCaIFNα4. Therefore, the dose of administration for one dog was determined by (body weight (kg))×(maltose paste containing 14 mg of BacCaIFNα4).

A BacCaIFNα4-containing maltose paste or BacCaIFNα4-free maltose paste was administered to each of the six dogs in the IFN administration group and control group, respectively, according to the following schedules.

Administration Schedule for the IFN Administration Group:
(1) BacCaIFNα4-free maltose paste was administered once a day after feeding (continued for seven days);
(2) followed by a seven-day interval; and
(3) BacCaIFNα4-containing maltose paste was administered once a day after feeding (continued for seven days).

Administration Schedule for the Control Group:
(1) BacCaIFNα4-free maltose paste was administered once a day after feeding (continued for seven days);
(2) followed by a seven-day interval; and
(3) BacCaIFNα4-free maltose paste was administered once a day after feeding (continued for seven days).

Gingival Index (GI), an index for gingivitis, was determined for each dog through schedules of (1) to (3) above to assess the time-course changes of gingival inflammation. The results are shown in Table 1.

TABLE 1

ADMINISTRATION EXPERIMENT (2) GI

|  | DURATION OF MAL ADMINISTRATION | | DURATION OF MAL AND IFNα ADMINISTRATION[b] | |
| --- | --- | --- | --- | --- |
|  | IFNα ADMINISTRATION GROUP | CONTROL GROUP | IFNα ADMINISTRATION GROUP | CONTROL GROUP |
| BEFORE ADMINISTRATION | 0.470 ± 0.126[a] | 0.518 ± 0.115 | 0.621 ± 0.042 | 0.683 ± 0.116 |
| 7 DAYS AFTER ADMINISTRATION | 0.510 ± 0.091 | 0.563 ± 0.111 | 0.452 ± 0.078 | 0.744 ± 0.113 |
| VARIATION[c] | 0.040 ± 0.076 | 0.046 ± 0.077 | −0.169 ± 0.062 | 0.062 ± 0.067 | n = 6,
[a]mean ± S.D.,
[b]maltose was administered to the control group alone without IFNα,
[c]the differences between seven days before and after administration are shown.
*differences between values are statistically significant (p < 0.01)
MAL: maltose
IFNα: BacCaIFNα4

The degree of inflammation was assessed by the method described below, which was modified from the known method of Löe and Sillness (Acta Odont. Scand., 1963; 21: 533-551). The degree of inflammation was classified into four stages and scored.

0: healthy gingiva without inflammation
0.5: gingiva with very mild inflammation along gingival crevice
1: gingiva with zonal inflammation along gingival crevice
2: gingiva with zonal inflammation along the entire gingival crevice or with inflammation over wide areas, accompanied by bleeding on probing For all the teeth, only buccal gingivae were examined. The total value was divided by the number of teeth tested and GI was determined. In the IFNα administration group, GI was 0.621±0.042 before the start of IFNα administration; however, GI was reduced to 0.452±0.078 up to seven days after start of administration. Decreased GI means alleviation of gingival inflammation. When compared with the GI variation in the control group during the same period, the decrease was significant. Furthermore, when compared with the case where maltose was administered alone, the reduction of GI after IFNα administration was significant.

It can be concluded that gingival inflammation was ameliorated by orally administering BacCaIFNα4 at a very low dose. This result suggests that the oral administration of a very low dose of BacCaIFNα4 is effective for suppressing gingivitis even in animals (dogs) with gingivitis that has already advanced to some extent. The progression of gingivitis can be prevented over a long period by further extending the duration of the very-low-dose oral administration.

Example 5

Administration Experiment (3)

A very low dose of BacCaIFNα4 was orally administered to beagles (female, 17 months old, 9 to 13 kg body weight) affected with gingivitis. The doses were 0 LU/kg body weight (control group), 0.25 LU/kg body weight (IFN0.25 group), and 25 LU/kg body weight (IFN25 group). A maltose paste was prepared to contain the indicated dose of BacCaIFNα4 and applied once a day on canine oral tissues, in particular, buccal gingivae after feeding continuously for 30 days. The preparation to be administered to the IFN25 group was prepared by combining 1 g of maltose with 395 µl of sterile distilled water, and adding 5 µl of BacCaIFNα4 ($5 \times 10^5$ LU/ml). The maltose paste (14 mg) contained 25 LU BacCaIFNα4. Therefore, the dose for one dog was determined by (body weight (kg))×(maltose paste containing 14 mg of BacCaIFNα4). Likewise, the preparation to be administered to the IFN0.25 group was prepared by adding 5 µl of BacCaIFNα4 ($5 \times 10^3$ LU/ml). A BacCaIFNα4-free maltose paste was administered once a day to the control group after feeding continuously for 30 days. GI was determined as an index for gingivitis for all groups up to 30 days after the start of IFN administration to assess the time-course changes of gingival inflammation. The result is shown in Table 2.

TABLE 2

| | ADMINISTRATION EXPERIMENT (3) GI | | |
|---|---|---|---|
| | IFNα 0.25 GROUP | IFNα 25 GROUP | CONTROL GROUP |
| BEFORE ADMINISTRATION | 0.851 ± 0.088[a] | 0.802 ± 0.111 | 0.813 ± 0.090 |
| 7 DAYS AFTER ADMINISTRATION | 0.634 ± 0.100 (−0.217 ± 0.020)[b] | 0.595 ± 0.126 (−0.206 ± 0.018) | 0.806 ± 0.099 (−0.008 ± 0.014) |
| 20 DAYS AFTER ADMINISTRATION | 0.601 ± 0.138 (−0.250 ± 0.057) | 0.516 ± 0.137 (−0.286 ± 0.102) | 0.738 ± 0.083 (−0.075 ± 0.025) |
| 30 DAYS AFTER ADMINISTRATION | 0.548 ± 0.143 (−0.304 ± 0.062) | 0.500 ± 0.167 (−0.302 ± 0.079) | 0.722 ± 0.099 (−0.091 ± 0.036) | n = 6,
[a] mean ± S.D.,
[b] the values in parentheses are differences with the ones before administration.
*differences between values are statistically significant ($P < 0.01$)
**$P < 0.05$
IFNα: BacCaIFNα4

As in the administration experiment described in Example 4, the GI value was gradually reduced during the administration period, and was significantly lower than that in the control group. There was no significant difference in the amelioration of inflammation between the doses 0.25 LU/kg and 25 LU/kg. This result suggests that the very-low-dose oral administration of BacCaIFNα4 is effective for suppressing gingivitis and the progression of gingivitis can be prevented over a long period by extending the duration of the very-low-dose oral administration.

INDUSTRIAL APPLICABILITY

The present invention is useful in preventing or treating periodontal disease in animals. The prevention and treatment of periodontal disease becomes an important objective in human as the aging society advances. Not only in human but also in animals bred for amusement in zoos as well as pet animals such as dogs and cats, aging is progressing as a result of improved breeding environments and such. Thus, the prevention and treatment of periodontal disease in animals have also become an important objective. The techniques of the present invention for preventing or treating periodontal disease are effective not only for human but also for animals. In particular, the oral compositions of the present invention can produce their effect when administered into the oral cavity. The oral compositions of the present invention can also be readily administered to animals by formulating them into feed or such.

The invention claimed is:

1. A method for treating periodontal disease in a dog, wherein said method comprises the step of administering interferon α at 0.25 to 25 Laboratory Unit (LU)/day/kg body weight and a maltose paste carrier on gingiva of the dog, which comprises administering interferon α once a day for at least 5 consecutive days.

2. The method of claim 1, which comprises administering interferon α once a day for at least 7 consecutive days.

3. The method of claim 1, which comprises administering interferon α once a day for 5 to 30 consecutive days.

* * * * *